United States Patent [19]

Wurm et al.

[11] Patent Number: 4,867,563

[45] Date of Patent: Sep. 19, 1989

[54] SPECTRORADIO-METER AND SPECTROPHOTOMETER

[75] Inventors: John H. Wurm; Lyle R. Middendorf; William W. Biggs, all of Lincoln, Nebr.

[73] Assignee: Li-Cor Inc., Lincoln, Nebr.

[21] Appl. No.: 788,084

[22] Filed: Oct. 15, 1985

Related U.S. Application Data

[63] Continuation of Ser. No. 717,594, Mar. 29, 1985, abandoned, which is a continuation of Ser. No. 413,496, Aug. 31, 1982, abandoned.

[51] Int. Cl.[4] .................................................. G01J 3/18
[52] U.S. Cl. .................................... 356/328; 356/334; 364/498
[58] Field of Search ............... 356/319, 326, 328, 332, 356/334; 364/498, 526; 250/239

[56] References Cited

PUBLICATIONS

Brown et al., *Canadian Journal of Remote Sensing*, vol. 6, No. 1, Jul. 1980, pp. 26–37.
Myrabo et al., *Applied Optics*, vol. 21, No. 15, Aug. 1, 1982, pp. 2855–2858.

*Primary Examiner*—F. L. Evans
*Attorney, Agent, or Firm*—Vincent L. Carney

[57] ABSTRACT

To provide sufficient sensitivity, spectral resolution and speed of measurement for field environmental measurements in a portable spectroradiometer, a silicon photodiode receives light: (1) having a bandwidth in the range of between 2 and 15 nm (nanometers) from a pivotable concave holographic diffraction grating within the wavelength range of between 250 and 1150 nm at a scanning rate in the range of 20 to 100 nm per second; (2) having stray light of high intensity and undesired frequencies and the shorter wavelength harmonics of the selected frequency range blocked by filters; and (3) having flux of at least 10 microwatts per square meter of diffuser plate for each nanometer of bandwidth. Automatic electrical zeroing is obtained by blocking all light once at the beginning of each scan, obtaining an electrical drift-related signal and using the drift signal to adjust the measured signal during the scan. Several different sensing interfaces can be used, including a quartz, light fiber probe having at least a 50% packing density and a cone angle of at least 24 degrees. The data and the programming storage is at least 30K bytes but the instrument uses no more than watts of power when the instrument is not scanning.

30 Claims, 11 Drawing Sheets

SPECTRORADIO-METER AND SPECTROPHOTOMETER

This application is a continuation of application Ser. No. 717,594, filed on Mar. 29, 1985, now abandoned, which is a continuation of application Ser. No. 413,496, filed on Aug. 31, 1982, now abandoned.

BACKGROUND OF THE INVENTION

This invention relates to apparatus and methods for measuring radiation or the characteristics of materials from the manner in which they react with radiation.

In one class of apparatuses and methods for measuring radiation or characteristics of materials from the manner in which they react with radiation, light of certain selected wavelengths is detected and the range of wavelengths is varied across a spectrum to provide an electrical signal corresponding to the light in each of the wavelength bands. The electrical output is then analyzed and is used to provide an indication of the nature of the light which has been received and, in some instances, the manner in which the light from a known source was altered by its interaction with a material, in which case the light is analyzed to determine the characteristics of the material.

In one type of prior art apparatus and method of this class, the detector is a photomultiplier that is controlled in temperature to provide a relatively high signal for a relatively low amount of flux. In such photomultipliers the electrical signal resulting from the light intensity available for usual studies is sufficiently strong for use.

Usually devices which measure the characteristic of light radiation from an external unknown source, which are referred to hereinafter as spectroradiometers, are used only for that purpose and devices which utilize light from a known source to determine the characteristics of a material interacting with the light are also stand-alone single-purpose units, referred to in this specification as photoradiometers.

The prior art apparatuses have several disadvantages such as: (1) they are relatively large; (2) they are expensive; (3) they require large amounts of power; (4) they are not portable nor easily used in the field, because of the large weight and power requirements; and (5) different stand-alone instruments must be used for spectroradiometry and photoradiometry, thus increasing the cost to the scientist.

SUMMARY OF THE INVENTION

Accordingly, it s an object of the invention to provide novel apparatuses and methods for measuring the spectral characteristics of light or characteristics of materials as determined by the interaction of the materials with different wavelengths of light.

It is a further object of this invention to provide a novel portable instrument for measuring light.

It is a still further object of this invention to provide a novel spectroradiometer which is portable and utilizes a small amount of power.

It is a still further object of this invention to provide a spectroradiometer which does not require temperature control and yet provides sufficiently precise measurements for use It is a still further object of this invention to provide a self-contained instrument for measuring light which is battery-operated and provides flexibility in obtaining measurements and providing data readout to the scientist.

In accordance with the above and further objects of the invention, a silicon photodiode in the light-measuring apparatus receives light having a bandwidth in the range of between 2 and 15 nm while scanning across the wavelength range of between 300 to 1150 nm at a rate within the range of 20 to 100 nm per second. Advantageously, the light is selected by pivoting a concave holographic diffraction grating and a rotating filter wheel, which filter wheel blocks lower wavelength harmonics of the light passed by the diffraction grating and other high intensity stray light. At the beginning of each scan, all light is blocked from the detector and the signal subtracted to provide automatic zeroing.

Depending on the frequency and bandwidth, there must be at least light flux density at the diffuser plate in the range of 10 microwatts to 1000 microwatts. The larger flux densities are required at the narrower bandwidths and shorter wavelengths.

To receive light under different conditions and for different applications, any of several different sensing interfaces may be used, such as a cosine diffuser, a light fiber probe with a cosine diffuser on its remote end, a light fiber conductor connected to a telescope at a remote distance and a light fiber probe receiving light from a sun-tracking heliometer. The light conductor is of quartz and has at least a 50% packing density and a cone angle of at least 24 degrees. The total efficiency of the lens coupling and the light conductor must be at least 25%.

The sensed signal may be read to meters or stored on cassettes within the instrument using a data processing unit having at least 30K bytes for data and programming storage which utilize no more than two watts of energy to maintain them when the instrument is not scanning. There are at least eight bit positions for each byte.

As can be understood from the above description, the apparatus and method for measuring light of this invention has several advantages, such as: (1) it is portable and may be used in the field; (2) it provides relatively precise measurements for spectroradiometry without temperature control; (3) it uses a relatively small amount of power; (4) it provides data readout in a number of different modes; (5) it is adaptable to remote measurement from a number of different sources such as through a cosine reflector, telescope, heliometer, spherical sensor or the like; and (6) it may be converted to a photoradiometer.

SUMMARY OF THE DRAWINGS

The above noted and other features of the invention will be better understood from the following detailed description when considered with reference to the accompanying drawings in which.

DETAILED DESCRIPTION

Figure 1:
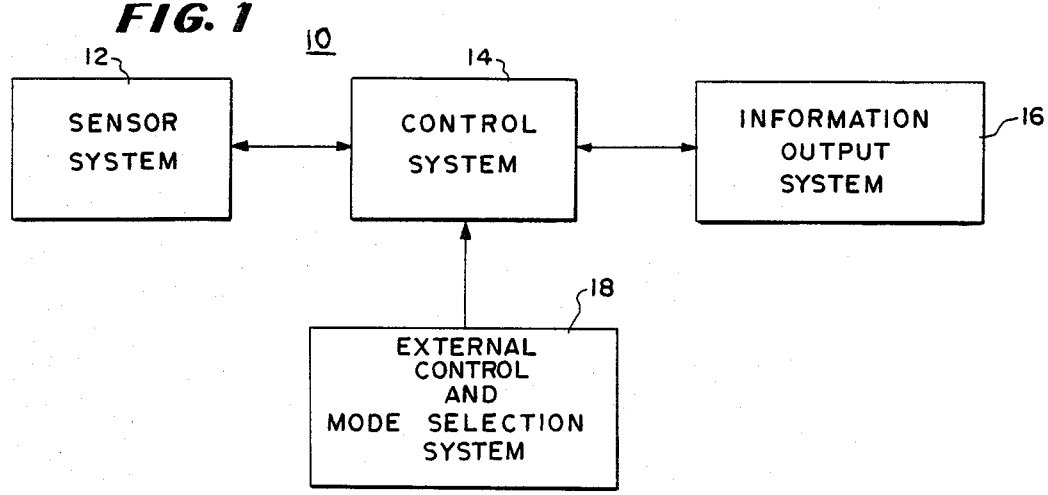
FIG. 1 is a block diagram of an embodiment of the invention.

In FIG. 1, there is shown a block diagram of a spectrographic instrument 10, specially adapted for spectroradiometric research and spectrophotometric chemical analysis, having a sensor system 12, a control system 14, an information output system 16 and an external control and mode selection system 18.

The control system 14 is electrically connected: (1) to the sensor system 12 to receive signals indicating spectroradiometric or spectrophotometric measurements; (2) to the external control and mode selection system 18 which provides information to it for calibration and for selection of functions to be performed; and (3) to the information output system 16 to which it provides the information in any of several different selected forms such as a strip-chart recording or the like.

The spectrographic instrument 10 is a portable, battery-operated, weatherproof unit which has self-sufficient control for data collection, analysis and display in the field when needed. It is adaptable to make measurements relating to spectroradiometry such as the infrared radiation or plant-cover measurements or in the alternative to perform spectrophotometric measurements such as protein analysis or the like.

Figure 2:
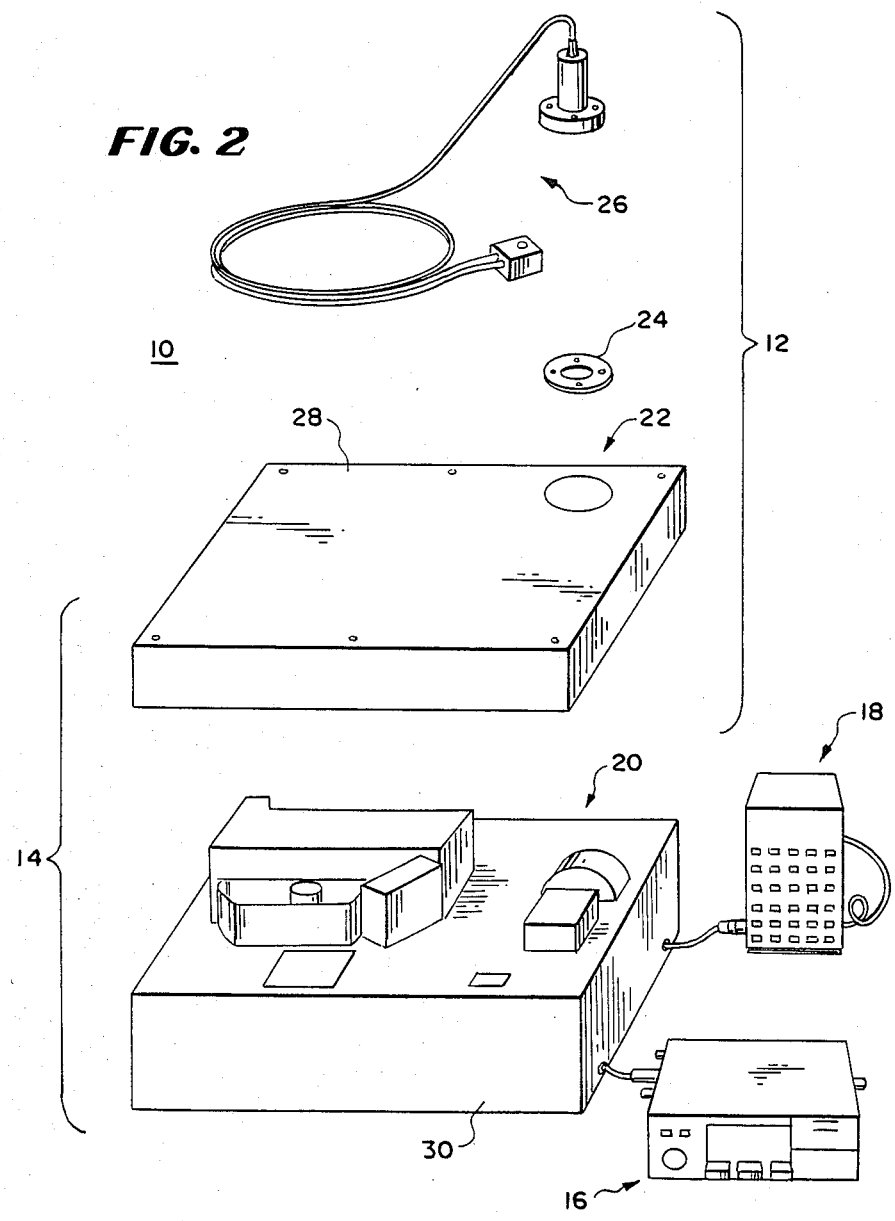
FIG. 2 is an exploded perspective view of the embodiment of FIG. 1.

In FIG. 2, there is shown an exploded perspective view illustrating the physical characteristics of the spectrographic instrument 10, with the control system 14 housed in its cabinet, one embodiment of information output system 16, one embodiment of external control and mode selection system 18 and two possible attachments forming a part of the sensor system 12. In the embodiment of FIG. 2, the information output system 16 is a cassette recorder into which data are recorded, but any other type of device could be used including a stripchart recorder or printout device. The external control and mode selection system 18 is a portable terminal although other types of external control devices can be used.

To sense radiation, the sensor system 12 includes certain radiation selecting optics 20, an adapter section 22, and any of a number of different radiation receptors. One possible radiation receptor is a cosine collector 24 shown in exploded position and another is a light fiber probe sensor, shown with its optics at 26. Still other sensors, not shown in FIG. 2, are a light source for a spectrophotometer, an integrating sphere, a remote cosine collector, a telescope and a spectrophotometric housing for basic chemical analysis work. The standard receptor is the cosine collector 24.

The light fiber probe sensor is quartz and may be connected to a telescope, a sun-tracking heliometer, a cosine diffuser, a scaler spherical receptor or the like. The light conductor fibers have at least a 50% packing density and a cone angle of at least 24 degrees. The packing density is the ratio of the area of light fiber to the total area of the light bundle.

The adapter section 22 is formed as a part of a cover 28 for the control system 14 and fits over a housing 30 enclosing the rest of the control system 14 so that with the cover 28 in place, a sealed control system is provided to which sensors, data input devices and data output devices may be attached. The housing 30 is weatherproof and provides a convenient portable container for the instrument.

To provide narrow bandwidth and good sensitivity, the sensor system 12 includes within the housing 30 a holographic grating and high quantum efficiency silicon photovoltaic device. With one monochromator, this portion of the sensor system 12 enables the bandwidth to be as low as 2 nm (nanometers) in wavelength at wavelength bands selected in the range between 250 to 850 nanometers or, with another monochromator, a bandwidth of 3 nm at wavelengths selected in the range of 300 to 1150 nanometers. Moreover, it is believed that bandwidths in this range of 2 nm to 15 nm are possible at a scanning rate in the range of 20 to 100 nm per second and within the wavelength range of between 250 and 1150 nm are possible.

The sensor system 12 cooperates with the control system 14 to remove drift by utilizing relatively fast scans, with the photovoltaic silicon device being mechanically covered at the beginning or end of each scan. Scans are averaged to provide an average reading. Drift is determined by comparison of signals generated at different times with the sensor covered. After being determined, the drift is removed from measurements to return the measurements to a zero value. Spectrum scanning is done in selected wavelength steps such as 0.5, 1, 2, 5 or 10 nanometer steps.

Data can be retained in internal memory or recorded on external memory. Internal memory can be as large as 36K bytes which provides a memory for 25 full scans of 400 data pairs of wavelength and data, each scan above one being averaged values. The sensed values from up to 256 scans can be averaged to provide the averaged values. The memory system for both data storage and programming storage should have at least 30K bytes for satisfactory operation. The instrument should require no more than two watts of power when the instrument is on but scanning is not occurring so the scanning motors are not operating.

The control system 14 can provide a data readout to the readout devices such as 16 in a selected one of any of several forms such as spectral irradiance or radiance, total irradiance or radiance, spectral photon flux density, photosynthetically active radiation between 400 to 700 nanometers, photosynthetic photon flux active radiation for wavelength ranges other than 400 density, photosynthetic irradiance, photosynthetically to 700 nanometers, illuminance, luminance and continuous monitoring of a selected wavelength.

The sensors and output devices are standard devices for which the control system 14 is adapted. The adaptation is at a minimum but: (1) some light sensors and light fibers are quartz so as to be able to receive ultraviolet light; and (2) light conductors have a packing density of at least 50% so as to be able to provide sufficient light flux to the sensor system. By providing light flux equal to that used by the sensor system, the light conductor input does not reduce the quality of the signal because of a lack of light flux passing from the sensor and the light conductor into the sensing systems. A standard keyboard is usable as the external control and mode selection system 18 and the readout systems may be analog or digital strip-chart recorders, plotters or printers or may be a standard cassette tape recorder. The total efficiency of the lens coupling and the light conductors should be at least 25 percent. Efficiency is the percentage of light flux, assuming full utilization of the field of view. The lens coupling is the coupling from the end of the light conductor to the monochromator.

Figure 3:
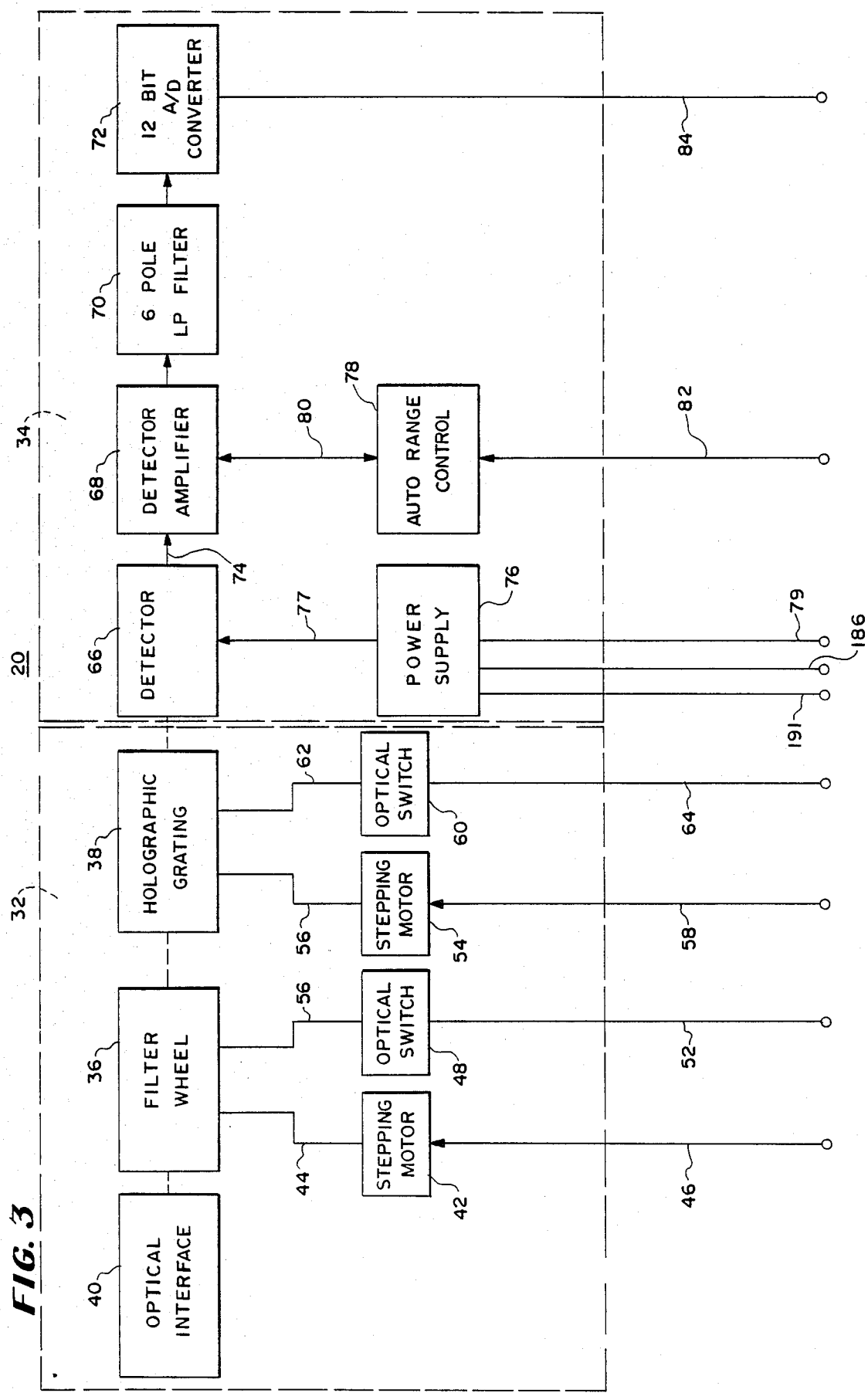
FIG. 3 is a block diagram of a portion of the embodiment of FIG. 1.

In FIG. 3, there is shown a block diagram of the portion of the light radiation selecting optics 20 of the sensor system 12 which is within the housing 30 (FIG. 2) having an optical section 32 and an electrical section 34. The optical section 32 selects the frequencies of light to be scanned, aids in automatically returning the measuring instruments to zero to remove drift and transmits the processed light to the electrical section 34. The electrical section 34 converts the light to an electrical signal, performs certain electrical processing and transmits a signal indicating the information in the light for further processing, recording and/or readout.

To perform optical processing, the optical section 32 includes as its principal parts a filter wheel 36, a holographic grating 38 and an optical interface 40. The optical interface includes a diffuser to provide diffused light to the monochromator.

The filter wheel 36 is optically aligned with the optical interface 40 and with the holographic grating 38 to receive light passing through the optical interface 40 and transmit the light through the holographic grating 38 into the electrical section 34 for detecting. The filter wheel 36 is adjusted into position to filter certain harmonics and noise or to block light entirely from the sensing devices for automatic drift removal. Light is entirely blocked to obtain a reference signal for the removal of drift from the system as will be explained more completely hereinafter.

To control the position of the filter wheel 36, a stepping motor 42 is mechanically connected to the filter wheel 36 through its output shaft indicated at 44 and receives pulses through a conductor 46 from the control system 14 (FIG. 1). The control system 14 receives indications of the position of the filter wheel 36 for reference purposes from an optical switch 48 which communicates with the filter wheel 36 through a communicating path 50 and supplies electrical signals indicating the position of the filter wheel 36 through a conductor 52 to the control system 14 (FIG. 1).

The control system 14 (FIG. 1) responds to instructions from the external control and mode selection system 18 (FIG. 1) for filtering or calibration to adjust the filter wheel 36 to the proper position as indicated by the optical switch 48. The filter wheel 36: (1) filters the higher frequency harmonics of light of the frequency that is to be passed to the holographic grating 38 since the holographic grating 38 passes such harmonics; and (2) filters certain high intensity strong light signals. The six-pole low-pass filter 70 (FIG. 3) filters frequencies above 100 hertz such as 120 cycles per second which may occur because of fluorescent light in the vicinity.

To select the frequency of light for the scan, a second stepping motor 54 is mechanically connected through a linkage 56 to the holographic grating 38 and is electrically connected to the control system 14 (FIG. 1) through a conductor 58 to control the angle of the holographic grating 38 and thus select frequencies. The position of the holographic grating 38 is detected by an optical switch 60 which communicates with the holographic grating 38 through a communication means 62 and provides signals on an output conductor 64 to the control system 14 indicating the position of the holographic grating 38.

In the preferred embodiment, the holographic diffraction grating 38 is a concave diffraction grating which is pivoted to pass light at any of several different positions between 300 to 1100 nanometers in wavelength. At each position, light of the selected wavelengths is transmitted with a bandwidth in the range of between 4 to 12 nm. The holographic grating scans throughout the positions at a scanning rate within the range of 20 to 50 nm per second.

The filter wheel 36 and holographic grating 38 permit sufficient light under the worst conditions in the ultraviolet range to be received by the detector 66. These conditions require at least 1,000 microwatts per square meter at the diffuser plate for each nanometer of bandwidth. The amount of flux is generally greater than this since the ultraviolet range is the range of light in which the flux is lowest. The holographic grating in the preferred embodiment has an f number (relative aperture) of less than 5. The relative aperture is the ratio of the effective aperture to the focal length.

To convert the light received from the optical section 32 to electrical signals, the electrical section 34 includes a detector 66, a detector amplifier 68, a six-pole low-pass filter 70 and a twelve-bit analog-to-digital converter 72.

The detector 66 is optically aligned with the holographic grating 38 of the optical section 32 to receive light and convert it to electrical signals which it conducts to the detector amplifier 68 through a conductor 74. The detector 66 is replaceable and may be a silicon photodiode, a photomultiplier tube or a lead sulfide detector, depending on the frequency which is desired. Each of these detectors has special advantages and the instrument is able to process signals in the frequency ranges best received by any of the detectors when the proper detector is selected and inserted.

However, under some circumstances, special advantages are obtained from a silicon photodiode detector with bandwidths of between 2 to 15 nm in the frequency range of 250 to 1150 nm in a system providing sufficient light flux. The light flux should be at least 0.001 watts per square meter of diffuser plate at 40 (FIG. 3) for each nanometer of bandwidth under worst conditions.

This combination of detector, flux and bandwidth enables sufficiently precise measurements to be obtained without special cooling and heating equipment and thus ultimately contributes to a low-weight, compact unit which may be portable and still provide satisfactory results for the scientist who uses it.

To provide power to the photomultiplier tube or lead sulfide detectors, a power supply 76 has its high voltage output electrically connected to the detector 66 through a conductor 77 for use with such detectors when inserted. It is also connected through any of a plurality of conductors indicated generally at 79.

Because of the different sensitivities of the detectors to different frequencies or because of the different intensities of different frequencies of light, the amplitude of the signal from the detector amplifier 68 representing the sensed light varies widely during the scanning. To accommodate this variation, an automatic range control 78 is electrically connected to the detector amplifier 68 through a cable 80 and to the control system 14 (FIG. 1) through a cable 82. The detector amplifier provides signals to the automatic range control 78 which controls its output amplitude in accordance with signals from the control system 14 received through the cable 82.

With this arrangement, a wide dynamic range is possible with good resolution. For example, data may be drawn or printed with different scales or a printer activated as selected in response to signals on cable 82 with the cooperation of the control system 14 (FIG. 1) without degeneration of resolution. Thus, the detector amplifier 68 is controlled to provide an adequate output while nevertheless keeping the signal within the dynamic range of the components of the equipment.

The output of the detector amplifier 68 is processed by the six-pole low-pass filter 70 and passed to the twelve-bit analog-to-digital converter 72 which provides an analog output on conductor 84 for recording or further processing in the control system 14 (FIG. 1).

Figure 4:
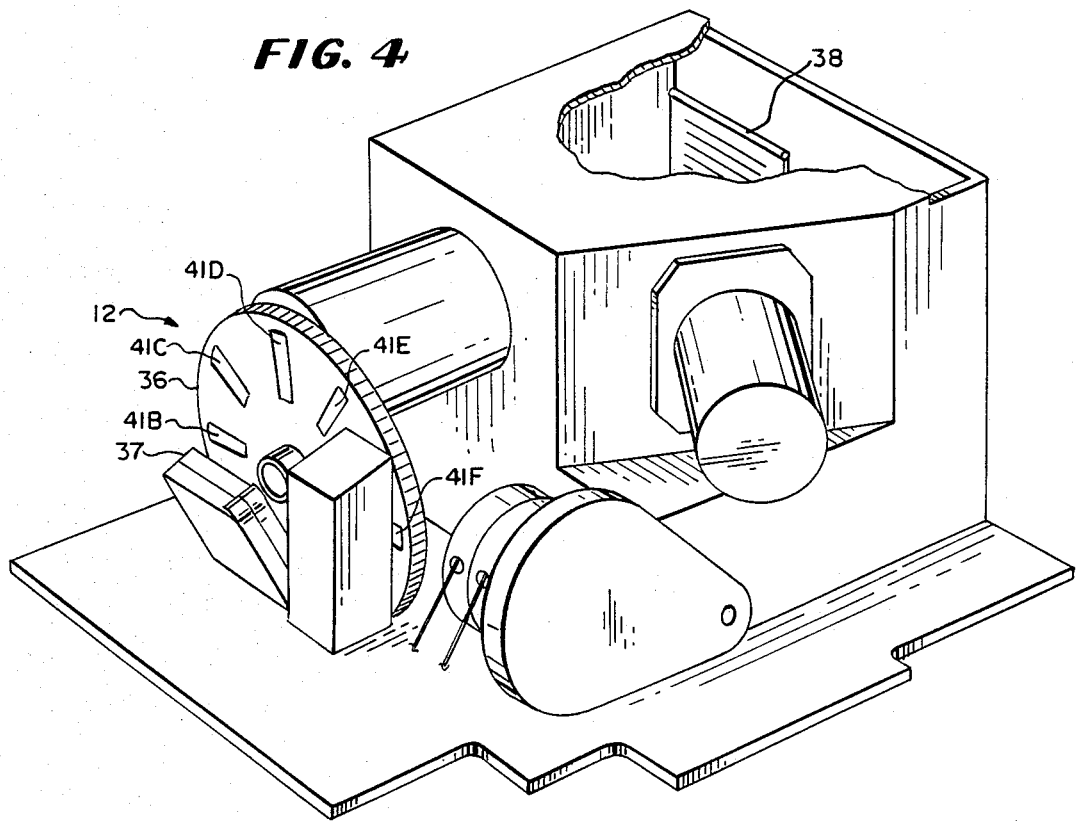
FIG. 4 is a simplified perspective view, partly broken away, of a portion of the embodiment of FIG. 1.

In FIG. 4, there is shown a simplified perspective view of a portion of the sensor system 12 having a mirror 37 for receiving light from the optical interface 40 (FIG. 3), a filter wheel 36, a casing 39 and a pivotable holographic diffraction grating 38.

As best shown in this view, the filter wheel 36 has a plurality of filters located around its central axis such as shown at 41B, 41C, 41D, 41E and 41F. This wheel rotates to pass light through a slit to the holographic diffraction grating 38. Both the filter wheel 36 and grating 38 are independently controlled by their own stepping motor to select a particular frequency of light to be passed and to confine the light being passed within a predetermined bandwidth to the fundamental frequency by blocking shorter wavelength harmonics and excessive stray light formed in the optical system.

One of the filter positions such as that shown at 41E is opaque and blocks all light. This position is used to provide a drift removal or zero electrical signal for automatic use in removing drift in the instrument. The other position each block lower harmonics from the selected frequency of the holographic grating as well as removing strong spectra of light that might be present at frequencies remote from the measured frequency.

Generally, the system of FIGS. 1-4 senses light as programmed by the operator either to: (1) measure light from a source such as the sun; or (2) measure light as it is affected by unknown characteristics of a medium to obtain information about the medium. The sensor is controlled to receive precise signal which may be processed for different readout devices at the convenience of the scientist under the control of the control unit 14 (FIG. 1). The system is designed for portable operation.

Figure 5:
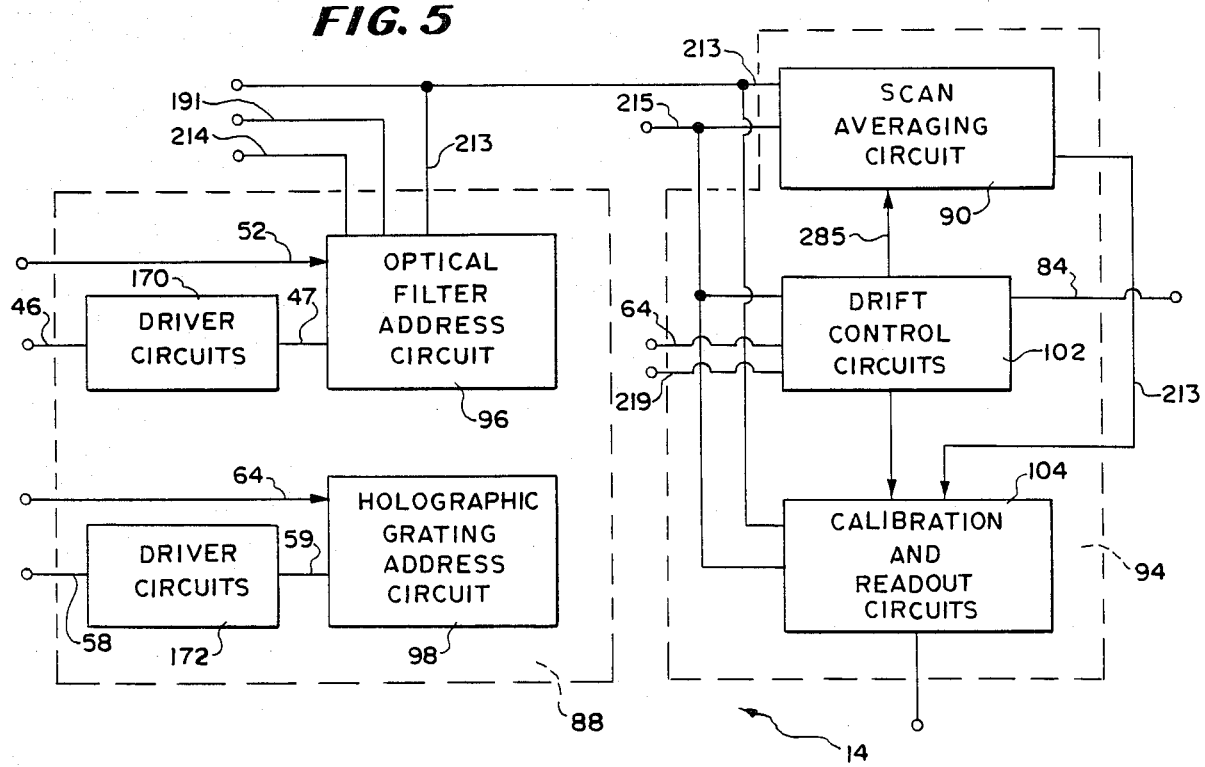
FIG. 5 is a block diagram of another portion of the embodiment of FIG. 1.

In FIG. 5, there is shown a block diagram of the control system 14 having an addressing system shown generally at 88 and certain data processing and readout circuits shown generally at 94.

The addressing circuit 88 controls the position of the holographic grating 38 (FIG. 3) and the filter wheel 36 (FIG. 3) and the data processing and readout circuits 94 receive the optical data from the twelve-bit analog-to-digital converter 72 (FIG. 3) and process it for readout to a user.

To control the scanning of frequencies and the removal of noise, the addressing circuit 88 includes an optical filter address circuit 96, a holographic grating address circuit 98 and two driver circuits 170 and 172 which have certain addresses set into them for scanning of the filter wheel 36 (FIG. 3) and the holographic grating 38 (FIG. 3) in a manner to be more fully described hereinafter.

The selections of the scans are made at a time set into the external control and mode selection circuits 18 or a series of times spaced apart at controlled intervals and at scan rates, averaging numbers and frequency ranges as set by the external control and mode selection system 18 (FIG. 1). The optical filter address circuit 96 is electrically connected to conductors 52 and 46 to receive signals from the optical switch 48 (FIG. 3) indicating the position of the filter wheel 36 and to actuate the stepping motor 42 to control the filter wheel 36 in accordance with a programmed scan or position.

The holographic grating address circuit 98 is connected to conductors 64 and 58 to determine the position of the holographic grating 38 from the optical switch 60 and to control the second stepping motor 54 to position the holographic grating 38. The structure of the address circuits is described hereinafter.

The data processing and readout circuits 94 include a scan averaging circuit 90, certain drift control circuits 102 and certain data conversion and readout circuits 104. Data from the twelve-bit analog-to-digital converter 72 (FIG. 3) are applied to the calibration and readout circuits 104 which are electrically connected to the drift control circuits 102 and to the scan averaging circuit 90 to remove baseline drift and to provide a data output in accordance with selected formats for strip-chart recorders or digital readouts or the like and with selected units of measurement.

Figure 6:
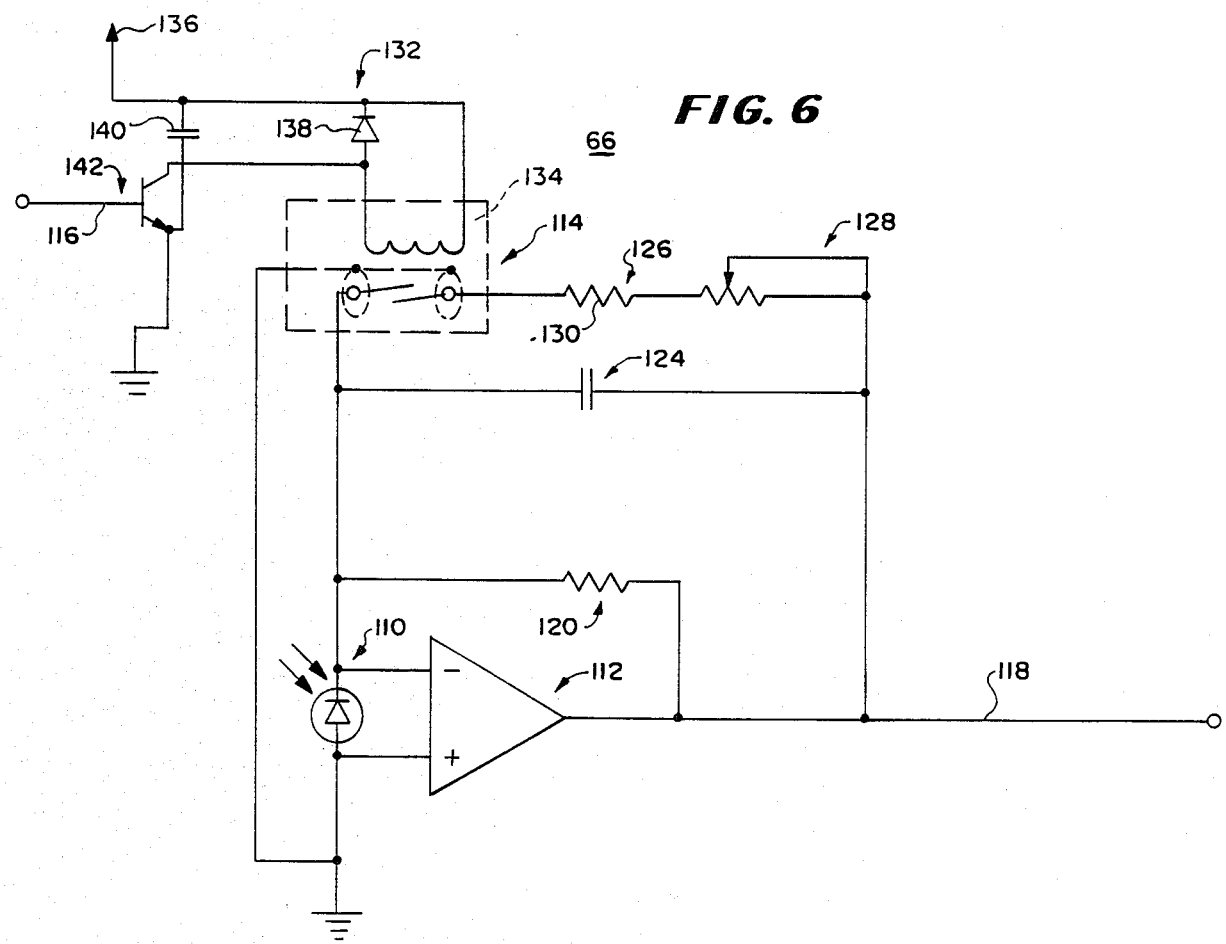
FIG. 6 is a schematic circuit diagram of a portion of the block diagram of FIG. 3.

In FIG. 6, there is shown a simplified schematic circuit diagram of the detector 66 having a silicon photodiode 110, an amplifier 112, and a range control circuit 114. The range control circuit 114 is controlled by signals on input conductor 116 to control the feedback from the output 118 of the amplifier 112 and to adapt the detector 66 for different ranges of intensity of light acting on the diode 110. The diode 110 is connected across the inverting and noninverting terminals of the amplifier 112.

To provide an output to conductor 118 as the light flux to the silicon photodiode varies, the anode of the silicon photodiode 110 is electrically connected to ground and to the noninverting input terminal of the amplifier 112 and the cathode of the silicon photodiode 110 is electrically connected to the inverting terminal of the amplifier 112 and to the range control circuit 114.

The output of the amplifier 112 is electrically connected to conductor 118. The range control circuit 114 includes three feedback paths, 120, 124, and 126. The feedback path 124 is capacitive and the feedback path 120 is resistive to form a circuit for stabilizing the amplifier 112. The feedback path 126 includes an adjustable resistor 128 for manually adjusting the amplitude of the feedback, a fixed resistor 130, and a reed relay control circuit 132 controlled by an input signal on conductor 116. The relay control circuit 132 includes a reed relay switch 134, a source of potential 136, a diode 138, a capacitor 140, and an NPN transistor 142.

To control the amount of resistance between the output 118 and the inverting input to the amplifier 112, the reed relay switch 134 is connected through the normally open relay switch between the resistor 130 and the inverting terminal of the amplifier 112. The electromagnetic control coil for the relay switch 134 is electrically connected at one end to the cathode of the diode 138, to a first plate of the capacitor 140 and to the source of potential 136. The other end of the coil is electrically connected to the anode of the diode 138 and the collector of the transistor 142.

The base of the transistor 142 is electrically connected to conductor 116 and its emitter is electrically grounded and electrically connected to the second plate of the capacitor 140 so that, when a positive pulse is applied to conductor 116, the transistor 142 conducts, causing a current to flow between source 136 and ground and thus closing the feedback path 126. When the conductor 116 is not receiving a positive potential, the feedback path 126 is opened.

Figure 7:
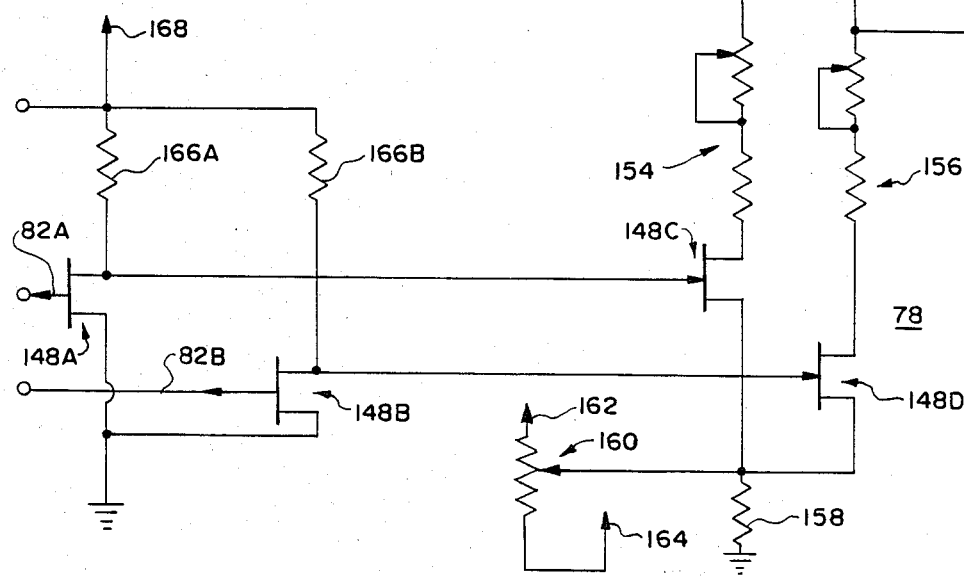
FIG. 7 is a schematic circuit diagram of another portion of the embodiment of FIG. 3.

In FIG. 7, there is shown a simplified schematic circuit diagram of the detector amplifier 68 and autorange control 78. The amplifier 68 has its non-inverting input terminal electrically connected to the output conductor 118 of the detector 66 (FIGS. 3 and 6) through a resistor 144 and has its output terminal electrically connected to the six-pole LP filter 70 (FIG. 3) through a conductor 146. The autorange control 78 is electrically connected in circuit with the output conductor 146 of the detector amplifier 68 and the inverting input terminal of the detector amplifier 68.

To control the output level of the detector amplifier 68, the autorange control 78 includes four junction-gate transistors 148A, 148B, 148C, and 148D, connected together to change the transfer function between the output conductor 146 and the inverting terminal of the amplifier 68 in accordance with one of two input signals on conductors 82A and 82B.

The inverting input terminal of the amplifier 68 is electrically connected to: (1) output conductor 146 through a resistor 150; (2) output conductor 146 through a capacitor 152; (3) one end of a first adjustable resistor 154; and (4) to one end of a second adjustable resistance 156.

The other end of the first adjustable resistance 154 is electrically connected through the junction gate transistor 148C to: (1) ground through a resistance 158; and (2) the center tap of a potentiometer 160. The second end of the second adjustable resistance 156 is electrically connected through the junction gate transistor 148D to ground through the resistor 158 and to the center tap of the potentiometer 160. The potentiometer 160 is connected at one end to a positive source of potential 162 and at its other end to a negative source of potential 164.

To select the feedback to the inverting terminal of the amplifier 68, the junction gate transistor 148A: (1) has its control electrode electrically connected to conductor 82A; (2) has its drain electrode electrically connected through a resistor 166A to a source of potential 168 and to the control electrode of the junction gate transistor 148C; and (3) has its source grounded.

The junction gate transistor 148B has: (1) its control electrode electrically connected to conductor 82B; (2) its drain electrode electrically connected to the source of potential 168 through a resistor 166B and to the control electrode of the junction gate transistor 148D; and (3) has its source grounded.

Consequently, the gain of the amplifier 68 is controlled by the selection of conductors 82A or 82B. This arrangement permits any of four different gains to be used, although in the preferred embodiment only three are used, gains of one, eight or sixty-four. The four gains are obtained by maintaining junction gate transistors 148C and 148D both closed or both open or selectively opening one and not the other. This can be done under the control of signals on conductors 82A and 82B.

Figure 8:
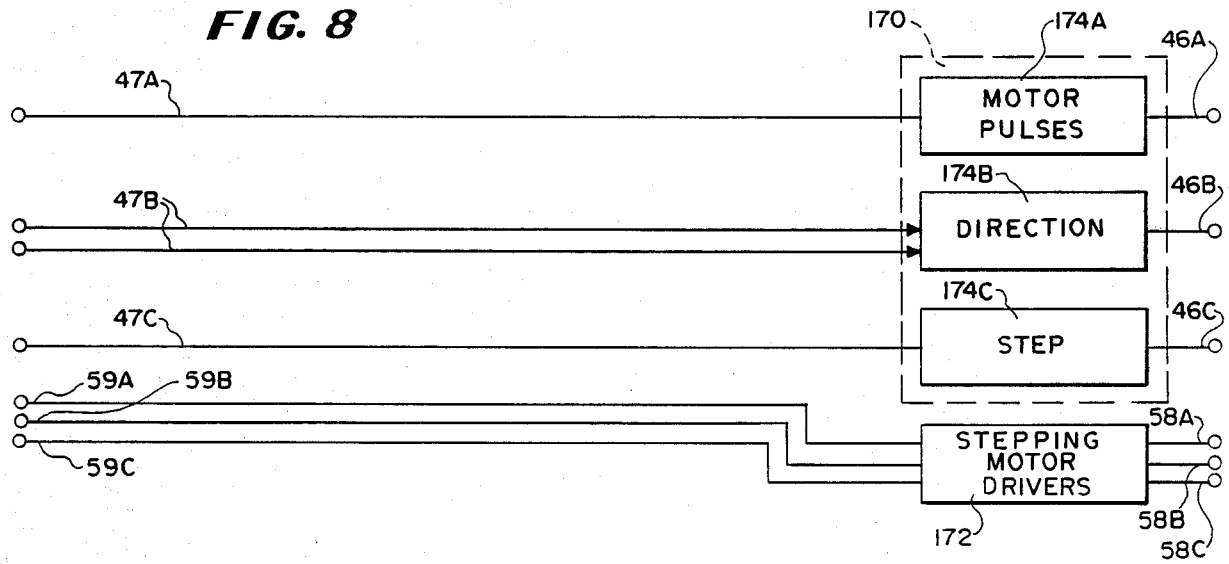
FIG. 8 is a block diagram of a portion of the embodiment of FIG. 1.

In FIG. 8, there are shown the driver circuits 170 electrically connected to receive signals from the optical filter address circuit 96 (FIG. 5) on conductors 47A–47C and provide signals to the stepping motor 42 for the filter wheel 36 (FIG. 3) on conductors 46A–46C and similar driver circuits 172 for receiving signals on conductors 59A–59B from the holographic grating address circuit 98 (FIG. 5) and providing signals to the stepping motor 54 for the holographic grating 38 (FIG. 3) on conductors 58A–58C.

The stepping motors 42 and 54 are conventional stepping motors purchased commercially and the driving signals to them are adapted to the commercial products and are generally in pulse form. For this purpose, the driver 170 includes a source of motor drive pulses 174A, a direction signal 174B and a signal to begin stepping 174C. The pulse circuits are generally transistor pulse circuits of a conventional sort as indicated by the manufacturers of the particular stepping motors. Similar circuits are provided for the stepping motor drivers 172.

Figure 9:
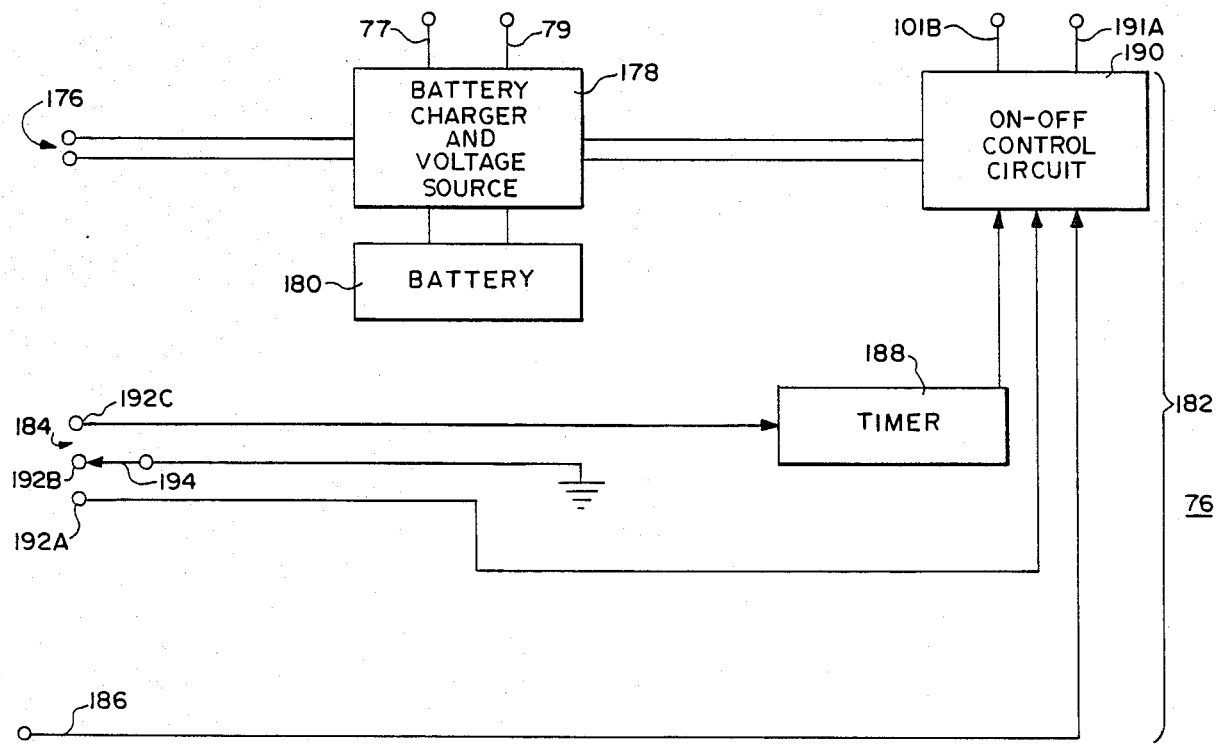
FIG. 9 is a block diagram of a portion of the embodiment of FIG. 1.

In FIG. 9, there is shown a block diagram of the power supply 76 electrically connected to the mains source of power at 176 to provide power at a high voltage through conductor 77 to certain of the detectors 66 (FIG. 3) or lower supply such as a positive five volts on a conductor 79 for use in the integrated circuits used throughout the system.

The power supply 76 includes a battery charger and voltage source 178, a storage battery 180, and an on-off circuit 182. The battery charger and voltage source 178 receives the mains power at 176, rectifies it and converts it to lower regulated DC potentials for use in the detectors and other circuits. It also supplies the battery 180 with a charging current to permit portable use of the instrument.

The battery charger and voltage source 178 is controlled by the control circuit 182 which includes an on-off switch 184, a control circuit actuation conductor 186, a timer 188, and an on-off control circuit 190. The on-off switch 184 is a three-throw, single-pole manual switch having an immediate scan position 192A, an off position contact 192B and a timer position contact 192C. The timer 188 is electrically connected to contact 192C and to one input of the on-off control circuit 190. Another input of the on-off control circuit is connected to a conductor 186 and a third to contact 192A.

With this arrangement: (1) when the armature or switch arm 194 is against contact 192B, the circuit is off; (2) when it is against contact 192A, it grounds that contact and the on-off control circuit which is electrically connected to it immediately initiates a single scan operation; and (3) when it is against contact 192C connected to a presettable-time timer 188, scans are initiated at preset times such as every 24 hours by the on-off control circuit 190 and the timer 188. Conductor 186 receives signals from the control circuit to generate scanning sequences under preset automatic control from the control circuit in a manner to be described hereinafter.

The timer 188 may be any standard timer consisting generally of counters actuated by a NOR-gate circuit which generate pulses when contact 192C is grounded and similarly contact 192A, when grounded, opens up a NOR-gate circuit within the on-off control circuit 190 to initiate a scanning sequence in a manner known in the art.

Figure 10:
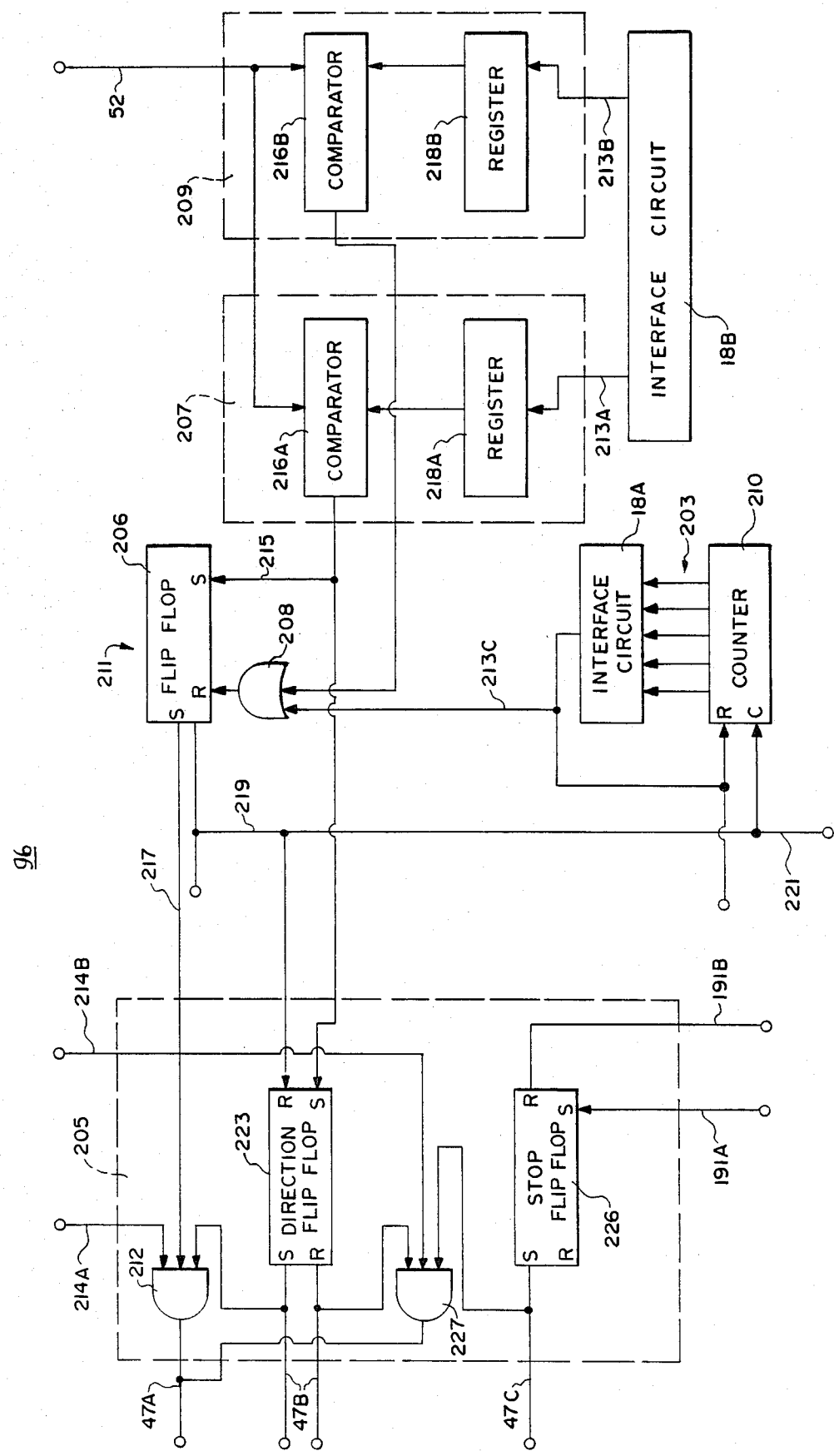
FIG. 10 is a block diagram of another portion of the embodiment of FIG. 1.

In FIG. 10, there is shown a logic circuit diagram of an embodiment of optical filter address circuit 96, having as its notable parts: (1) the input conductor 52 from the optical switch 48 (FIG. 3); (2) the output conductors 47A-47C leading to the driver 170 for the stepping motor 42 (FIG. 3); (3) interface circuits 18A and 18B for selecting the wavelengths; (4) a motor control circuit 205; (5) low and high wavelength value circuits 207 and 209; and (6) a scan control circuit 211.

The high and low wavelength circuits 209 and 207 are both electrically connected to conductor 52 to receive signals indicating filter position and to conductors 213A and 213B, from which they receive indications of the wavelength range limits. At a low wavelength consistent with an input signal applied through conductor 213A to the low wavelength circuit 207, the low wavelength circuit 207 provides a set signal on a conductor 215 to the scan control circuit 211, which includes a flip-flop 206, an OR gate 208, the interface circuit 18A, and a counter 210. This signal is provided to the set terminal of the flip-flop 206, causing a signal to be applied to its set output terminal for transmission on conductor 217 to the motor control circuit 205 to start the scanning from filter position to filter position by filter wheel 36 (FIG. 3). At certain filter positions the grating scans selected ranges of frequencies as described hereinafter.

The counter 210 is electrically connected through conductor 219 to count the number of scans and provide them through conductor 221 for recording as well as applying them to the count input terminal of counter 210. The output conductors of counter 210 are electrically connected through the interface circuit 18A of the manual control and adjustment section 18 (FIG. 1) to permit selection of one of the outputs of counter 210 through a conductor 213C.

The OR gate 208 has its output electrically connected to the reset input terminal of the flip-flop 206 and has its inputs electrically connected to conductor 213C and to the output of the high-level circuit 209 so that, when the preset number of counts have been completed after the motor is started, the flip-flop 206 is reset, applying a signal through conductor 217 to stop the scanning motor, and a pulse is applied to counter 210 to count one scan. Thus the motor is started when the filter wheel is at a predetermined high frequency and operates until the lowest frequency of the scan is reached and this process is repeated until a predetermined number of scans between the high and low frequencies as determined by counter 210 have been completed.

To detect the predetermined short wavelength to start the scan, the low-value circuit 207 includes a comparator 216A and a register 218A. The comparator 216A receives frequency information through conductor 52, indicating the position of the filter wheel 36 (FIG. 3), and on the other input receives signals from register 218A. Register 218A receives information from the interface circuit 18B, indicating a preset starting short wavelength at the start of the scan.

Thus, at the start of each scan, when the stepping motor 42 brings the filter wheel 36 to the start frequency, this frequency is indicated on conductor 52 as the frequency indication from register 218A in comparator 216A, resulting in an output signal on conductor 215. All of these signals are, of course, digital at this point, the filter position measurements having been converted to a digital signal by the input circuitry.

The long-wavelength circuit 209 includes similar components acting in a similar manner and for this purpose includes a comparator 216B and a register 218B. The long-wavelength end of each scan is applied to the register 218B from the interface circuit 18B through conductor 213B for eventual comparison with the filter wheel position signal received on conductor 52.

The motor control circuit 205 includes an AND gate 212, a flip-flop 223, a flip-flop 225 and an AND gate 227. The step flip-flop 225 receives a signal on conductor 191A (FIGS. 3 and 9) from the on-off control circuit when measurements are to be made and a signal on conductor 191B when the instrument is turned off. When the flip-flop 225 has been set by a signal on conductor 191A to its set input terminal and no signal has yet arrived at its reset input terminal from conductor 191B, it provides an output to conductor 47C and to one of three inputs of the AND gate 227 to provide a step signal to the motor drive circuit 170.

The direction flip-flop 223 has its set input terminal electrically connected to conductor 215 from the low-wavelength circuit 207 to indicate scanning in the scanning direction on one of the conductors 47B and has its reset input terminal electrically connected to conductor 213C to reset the flip-flop and apply a potential to the other of its conductors 47B at the end of a scan so as to return the filter wheel to its zero position. The reset output of the flip-flop 223 is electrically connected to a second of the three inputs to the AND gate 227 and a third input is electrically connected to a source of rapid pulses through conductor 214B. The output of the AND gate 227 is electrically connected to conductor 47A to step the motor at a rapid rate in a direction opposite to the scan direction to return it for another scanning operation.

To apply scanning pulses at a preset rate, the AND gate 212 has one of its three inputs electrically connected to conductor 214A to receive pulses at a set rate, a second of its input pulses electrically connected to the set output terminal of the flip-flop 206 to receive an indication at the start of a scan equivalent to the preset low wavelength for the scan and a third of its inputs electrically connected to the set output terminal of the direction flip-flop 223 to receive a signal when the stepping motor is prepared to step in the scan direction. As the addresses are sequenced to the comparators 216A and 216B, signals are provided to turn the stepping motor 42 (FIG. 3) through conductor 46 to move the filter wheel 36 (FIG. 3) to the selected frequency in response to comparisons of an optical code on conductor 52 from the optical switch 48 (FIG. 3) with the codes of the end points set in registers 218A and 218B.

In this manner, the filter wheel 36 is moved from position to position in accordance with clock signals, passing through the optical filter address circuit 96 to perform the function of blocking certain frequencies. In the preferred embodiment, higher harmonic frequencies of those to be selected by the holographic grating 38 (FIG. 3) are blocked by synchronizing the position of the filter wheel 36 with the position of the holographic grating 38.

The holographic grating address circuit 98 is substantially the same as the optical filter address circuit 96 except that the input conductor to its register is conducted by conductor 64 from the optical switch 60 (FIG. 3) and the output conductor to its stepping motor 54 (FIG. 3) is conducted by conductor 58. The range of wavelengths in each scan is set in interface circuits similar to 18B and the number of scans is set in an interface circuit such as 18A. In the preferred embodiment, for certain positions of the filter wheel, the grating address circuit 98 is programmed to provide pulses to its stepping motors to scan a preset frequency range.

At the end of each scan, a pulse from the reset terminal of flip-flop 206 on conductor 221 is counted and, at the programmed number of scans in interface 18A as counted by counter 210, a pulse is provided to conductor 213C, indicating the end of a series, and measurements are averaged for the scans in a manner to be described hereinafter.

Figure 11:
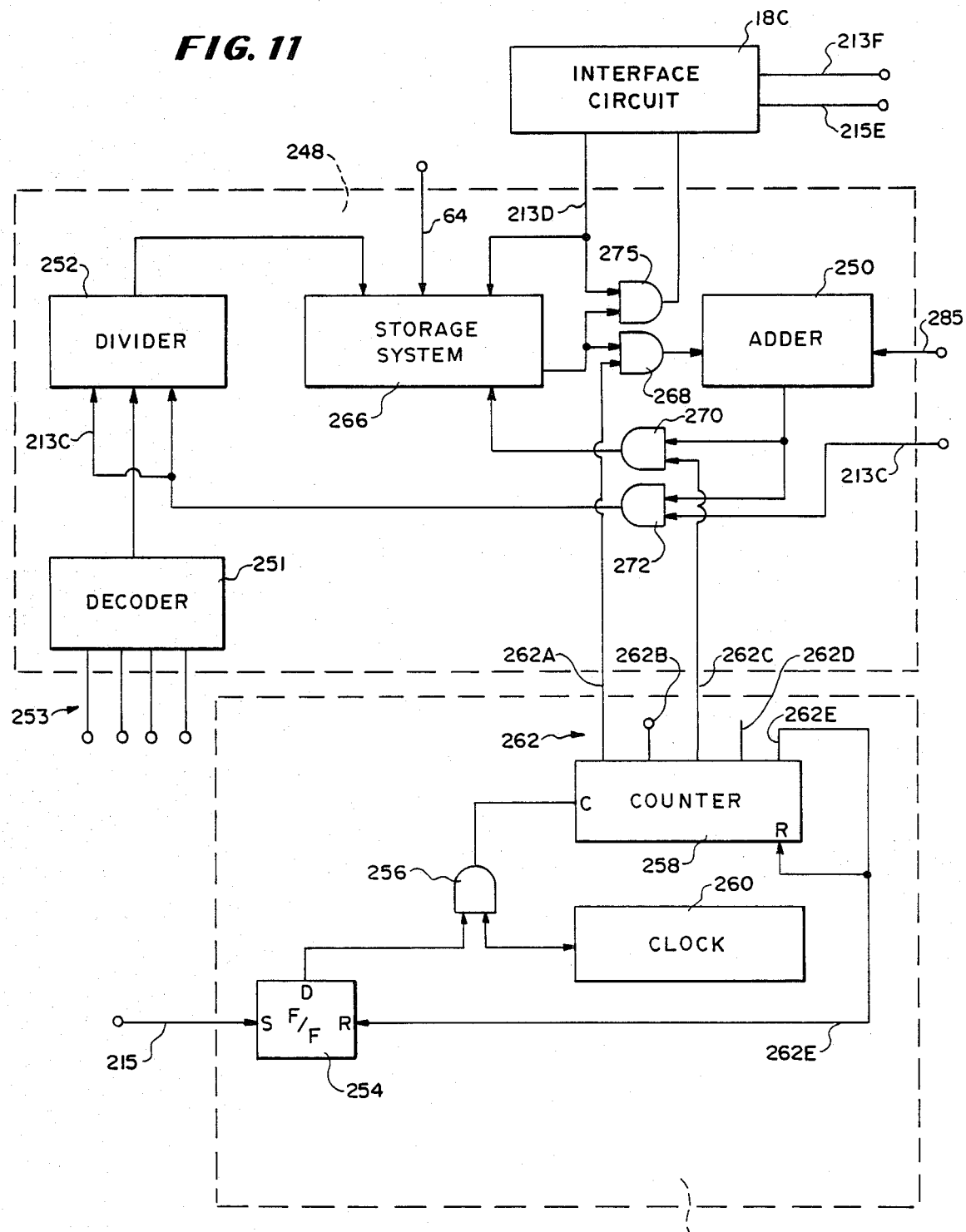
FIG. 11 is a block diagram of still another portion of the embodiment of FIG. 1.

In FIG. 11, there is shown a block diagram of the scan averaging system 90, having an interface unit 18C, a timing control system 246 and a controlled unit system 248.

The timing control system 246 is a circuit which provides timing signals to the controlled unit system 248 upon receiving an actuation signal on conductor 215. The timing signals are provided through a plurality of conductors 262 to the controlled unit system 248 to cause that system to calculate an average of data applied to it through a conductor 84 from the analog-to-digital converter 72 (FIG. 3). The interface circuit 18C, which includes switches that may be selected, provides signals at timed intervals to the controlled unit system 248 to read the average data from a series of scans to a selected unit.

The timing control system 246 includes a flip-flop 254, an AND gate 256, a counter 258 and a source of clock pulses 260. When the actuating signal on conductor 215 is received, the flip-flop 254 is set and an output is provided to one of the two inputs to AND gate 256. The other input to the AND gate 256 receives pulses from the clock pulse generator 260.

The output from the AND gate 256 causes the counter 258 to count from output conductor 262A to output conductor 262E and thus provides pulses in sequence to the controlled unit system 248 through conductors 262. The frequency of the clock pulse generator 260 is selected so that the output signal from the counter 258 occurs at intervals related to the sequence of events that is to be controlled upon receiving a signal on conductor 215. Thus, data are added, divided and stored as an average in the controlled unit system 248 for readout later under the control of the interface circuit 18C. The time needed for those events may be set for each action by selecting the proper frequency of the clock 260 and the counter 258.

To terminate the sequence of events, an output conductor 262E is connected to a final stage of the counter 258 to provide a pulse to the reset input terminal of the flip-flop 254 and of the counter 258 to reset them.

The controlled unit system 248 includes a decoder 251, a divider 252, a storage system 266, and an adder 250. The adder is connected to conductor 285 to receive scan data on one input from the drift control circuit 102 (FIGS. 5 and 12) and is connected through an AND gate 268 at its other input to add the total from previous scans, if any. Its output is electrically connected through an AND gate 270 to the storage system 266 to store the sum of each scan in a series and to divider 252 through an AND gate 272 to transfer the total of the scans to the divider 252 to be divided by the total number of scans to form an average.

The decoder 251 receives conductors 253 from counter 210 (FIG. 10), indicating the number of scans, and applies this number to divider 252, which is connected to conductor 213C from interface 18C, indicating the end of a series of scans, to cause the divider 252 to the sum of readings at corresponding data points for each scan by the number of scans and apply this average to the storage system 266 in a manner known in the art.

The static signal on conductor 213 causes the total of the readings from each scan to be applied from the output of the adder 250 through AND gate 272 to the divider. Each scan includes a series of readings indicated by positions of the grating 38 (FIG. 3) and these are indicated in storage by signals forming a time base received on conductor 64 from optical switch 60 (FIG. 3).

The output conductors 262 first open AND gate 268 to adder 250 for transfer of the total from previous scans for each frequency to adder 250 for addition to last scan data on conductor 285 and later transfers the sum back to the storage system 266 through gate 270 under the control of conductor 262C. While one gate is shown, in practice a series of gates are used to transfer data, reading by reading, as the counter 258 is sequenced stage by stage.

The interface circuit 18C is connected to the output of AND gate 275 to receive data from storage system 266 and transfer it to one of output conductors 213F for transfer to the calibration and readout circuit 104 (FIG. 13) in response to a signal on conductor 215E to the interface circuit and on conductor 213D to the storage system.

Figure 12:
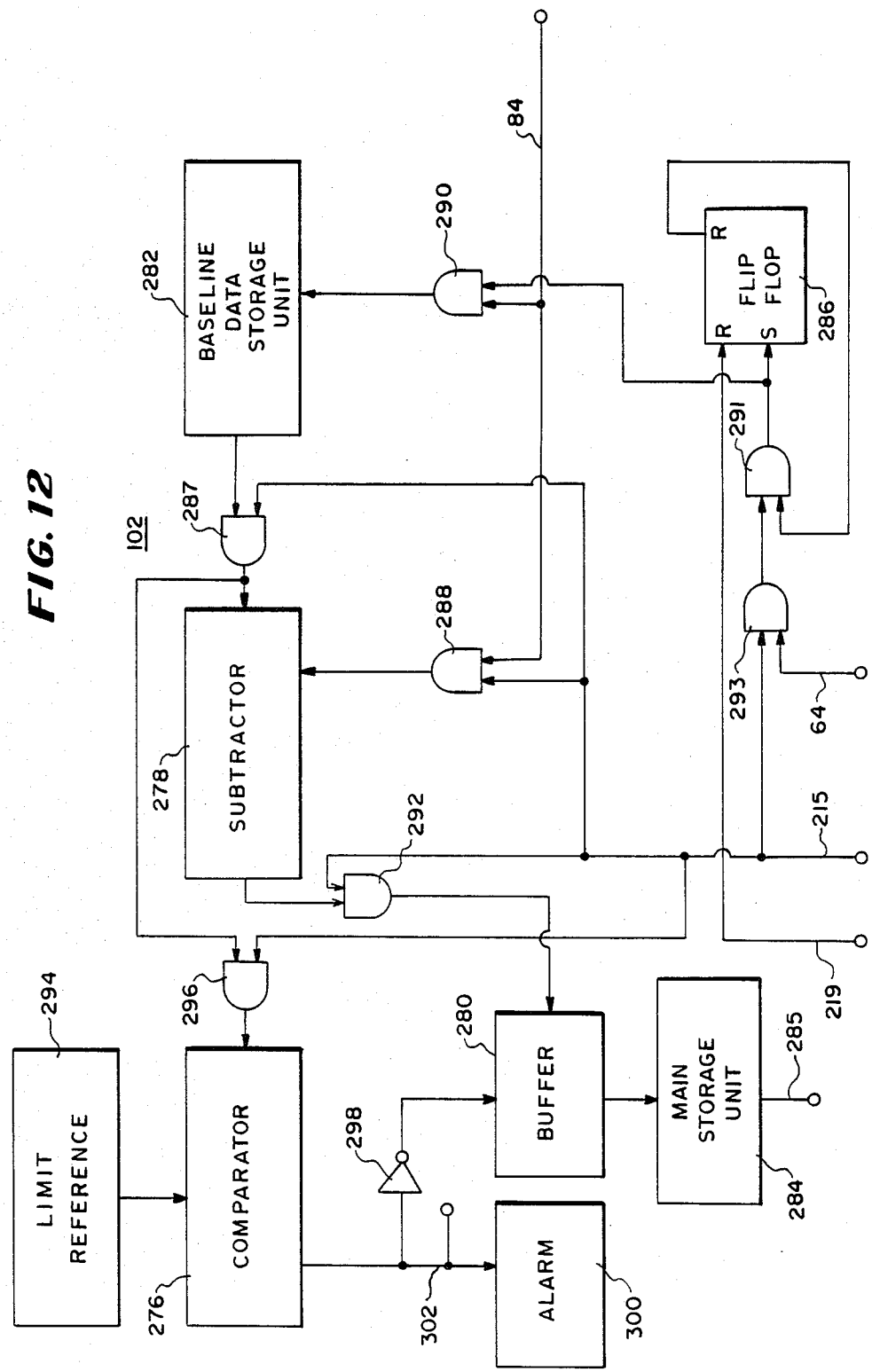
FIG. 12 is a block diagram of still another portion of the embodiment of FIG. 1.

In FIG. 12, there is shown a block diagram of the drift control circuit 102, having a comparator 276, a subtractor 278, a buffer 280 and a baseline-data storage unit 282.

To transfer a baseline signal to the baseline-data storage unit 282, a flip-flop 286 has its reset input terminal electrically connected to conductor 219 and its set input terminal electrically connected to the output of an AND gate 291. One input of the AND gate 291 is electrically connected to the reset output terminal of flip-flop 286 and the other input is electrically connected to the output of an AND gate 293. One input of the AND gate 293 is electrically connected to conductor 215 and the other to conductor 64 to set the flip-flop 286 at the beginning of each scan and reset it after the baseline position, which is the first data word of each scan.

The AND gates 288 and 290 each have one of their two input terminals connected to conductor 84 to receive input data from the twelve-bit analog-to-digital converter 72 (FIG. 3). The AND gate 288 has the other of its two input terminals connected to conductor 215 and its output connected to subtractor 278; and AND gate 290 has its other input electrically connected to the output of AND gate 291 and its output connected to the baseline-data storage unit 282.

The baseline-data storage unit 282 is connected to one of the inputs of subtractor 278 through AND gate 287 and stores the baseline digital value for subtraction from each digital reading during one scan. For this purpose it is a static register and the AND gate 287 has one input connected to its output and its other connected to conductor 215. In practice the AND gates 287 and 288 may be replaced by parallel arrays and the signal on conductor 84 may be a parallel word applied from the analog-to-digital converter 72 (FIG. 3).

With this arrangement, the first data word of each scan which occurs when the optical unit is covered to prevent light from reaching it passes to the baseline-data storage unit 282 where it is stored and transmitted to one input of subtractor 278 and each of the data words from the scan is transmitted to the other input of the subtractor 278.

To subtract the baseline from the data, the baseline-data storage unit 282 is electrically connected to one input of the subtractor 278 through and AND gate 287 and conductor 84 is connected through the AND gate 288 to the other input of the subtractor 278. When the flip-flop 206 (FIG. 10) is set, the subtractor 278 subtracts the baseline stored in baseline-data storage unit 282 from the incoming data and transfers that information to the buffer 280.

To perform that transfer, and AND gate 292 has one input electrically connected to the output of the subtractor 278 and the other input electrically connected to conductor 215, the output of the AND gate 292 being connected to the input of the buffer 280. The output of the buffer 280 is electrically connected to the main storage unit 284. The buffer 280 contains one scan of data, which is read from the buffer into the main storage unit 284, to which it is electrically connected.

To eliminate scans when an irregular baseline indicates error, the drift removing circuit 102 includes a comparator 276, a limit-reference value 294, and AND gate 296, an inverter 298 and an alarm 300. One of the inputs of the AND gate 296 is electrically connected to the output of AND gate 287 and the other of its two inputs is connected to conductor 215, the output of the AND gate 296 being connected to one of the two inputs of the comparator 276 so that the first word of a scan is applied to the comparator 276. This word, which represents a state of the detector when a light-blocking screen is across it, is compared with a limit reference 294 and, if it is beyond a predetermined range, the comparator applies a signal to the alarm 300 and to the buffer 280 through the inverter 298.

In this condition, the buffer 280 erases the information. If the comparator 276 indicates a close comparison between the final word after it has been subtracted from the first word stored in the baseline-data storage unit 282, then the buffer 280 reads the scan data into the main storage unit 284.

With this arrangement, the first word indicating the baseline at the beginning of a scan as stored in baseline-data storage unit 282 is subtracted from the final word representing the same quantity and the difference is compared to a limit reference 294. If it falls within the limit to indicate a close comparison, the scan is stored in the main storage unit from the buffer but, if the difference is large, indicating a discrepancy, the buffer is read out and that data scan is eliminated from the data. The signal is also applied to conductor 302 to change the number which is used in averaging the scans by reducing it by one. In one embodiment, the faulty data are not eliminated but instead a statement is printed stating that there is a discrepancy.

Figure 13:
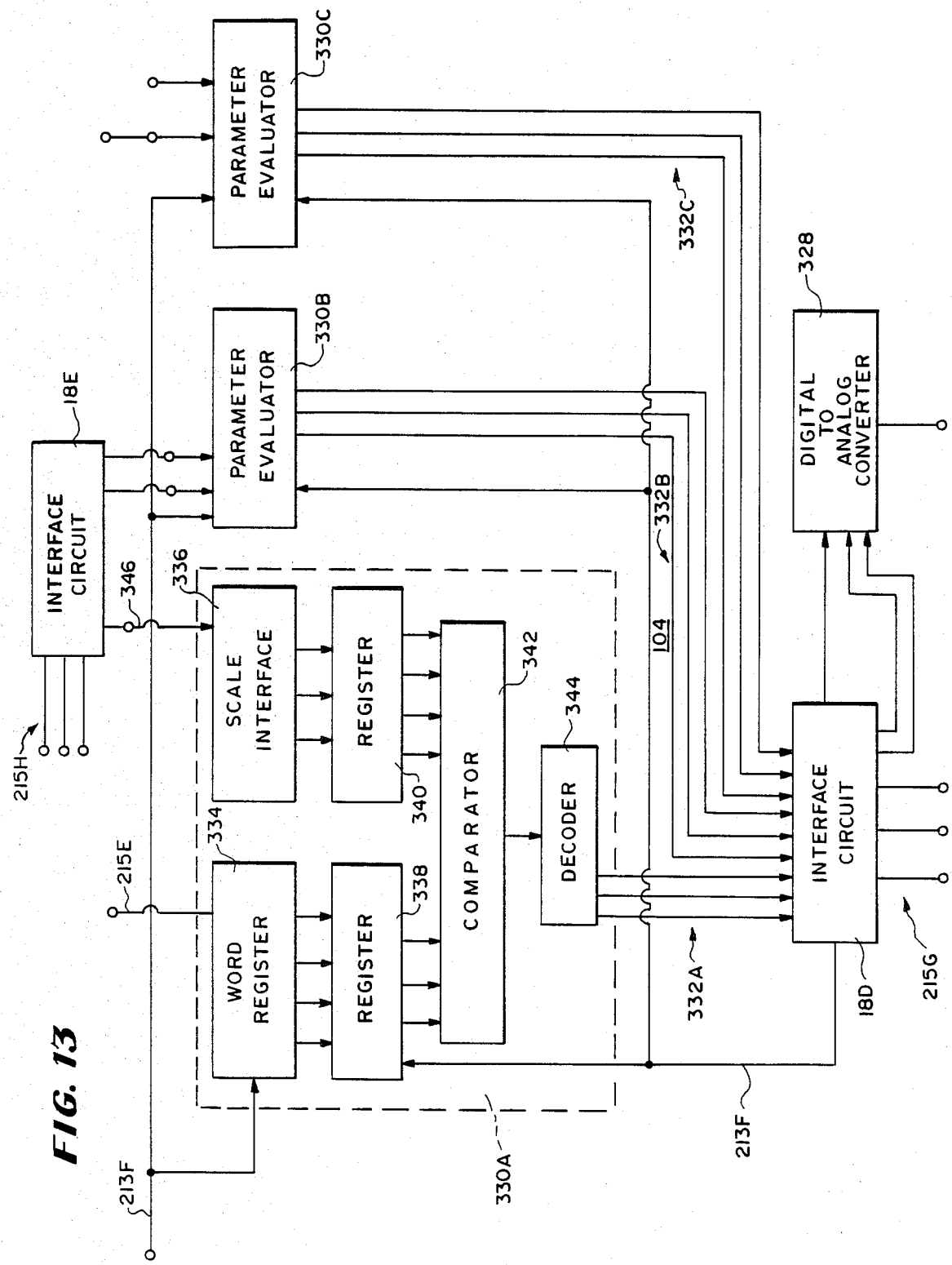
FIG. 13 is a block diagram of still another portion of the embodiment of FIG. 1.

In FIG. 13, there is shown a block diagram of the calibration and readout circuit 104, having interface circuits 18D and 18E, a digital-to-analog converter 328 and three parameter evaluators 330A, 330B and 330C, each being connected to receive the readout of the average value of a plurality of scans of each of a selected series of wavelengths from the storage system 266 (FIG. 11) on conductor 213F. Each of the parameter evaluators 330A–330C provides output signals when the value represented by the code on conductor 213F is a predetermined value and that output is provided on a particular one of the outputs 332A–332C.

There may be as many parameter evaluators as necessary and normally for a single quantity on conductor 213F there are a plurality of parameter evaluators sufficient in number to indicate different incremental levels of the quantity that is being received.

The parameter evaluator 330A is the same as the parameter evaluators 330B and 330C in structure and has a word register 334, a scale interface 336, a first register 338, a second register 340, a comparator 342 and a decoder 344. The scale interface 336 has a value set into it by switches or by writing it into a memory or by energizing an ROM or the like. Switches may be thrown as in the other interface circuits to provide a particular code output to the register 340 indicating a value.

The word register 334 receives signals on conductor 213F indicating the quantity being read and provides its output in a compatible code to the register 338. The first and second registers 338 and 340 are electrically connected to the first and second inputs of the comparator 342 so that, when the value in register 338 equals the value set in the register 340, a signal is provided to decoder 344 which indicates a calibrated output value to the interface 18D on one of a plurality of conductors 332A–332C. Thus, the output conductors 332A–332C indicate different levels of the quantities that are being measured and indicated by the conductor 213F. The interface circuit 18D resets the registers 338 and 340 upon providing a signal to the output conductors 215G to a selected digital peripheral or to the digital-to-analog converter 328 which provides an analog signal on its output.

The scale interface 336 is set using a series of known input light values to the optical interface 40 (FIG. 3) of the sensor system 12 (FIG. 1) from a known source and setting each of the scale interfaces 336 in each parameter evaluator 330A–330C to provide a digital signal corresponding to known values for a corresponding input 213F. The decoders are set to provide the numerical indication of the input.

To accomplish this result, an input light of known frequency and intensity is applied to the sensor system and a corresponding decoder which provides a code equal to that intensity is set. The input 346 to the scale interface is electrically connected to be energized at the position of the grating 38 (FIG. 3) corresponding to this frequency and the scale interface is set to provide the same value code output as measured on conductor 213F for application to the corresponding word register 334.

Figure 14:
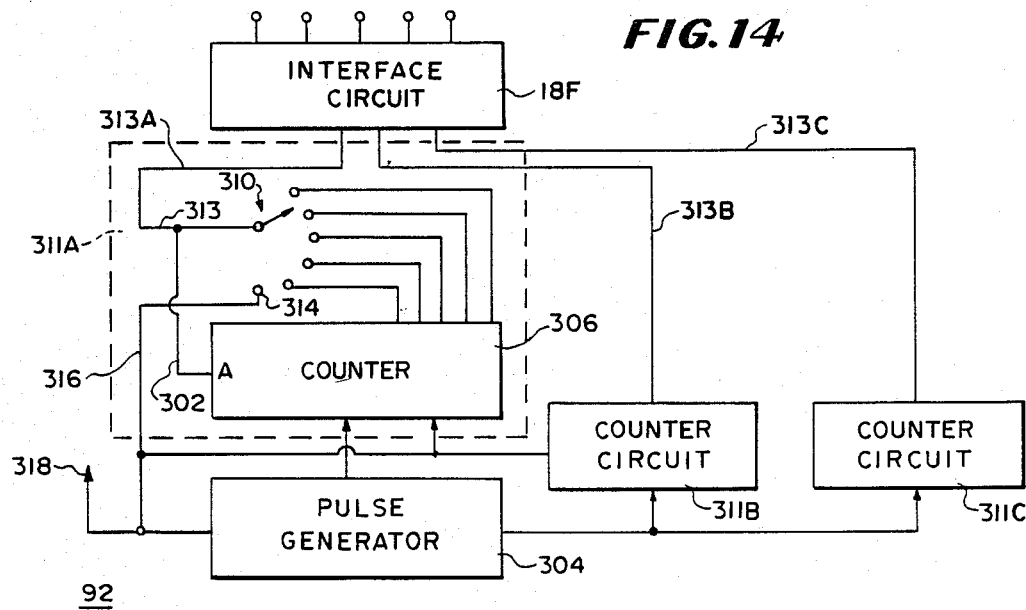
FIG. 14 is a block diagram of still another portion of the embodiment of FIG. 1.

In FIG. 14, there is shown a block diagram of a timer circuit 92, which is part of the external control and mode selection system 18, having a pulse generator 304, a plurality of counter circuits, three of which are shown at 311A–311C, an interface circuit 18F and a switch 310.

To select pulses with different time increments for application to other circuits, the interface circuit 18F is electrically connected through a corresponding one of the conductors 313A, 313B or 313C to a corresponding one of the counter circuits 311A, 311B or 311C. The pulse generator 304 has its output electrically connected to each of the counters to supply pulses thereto and to supply a source of DC potential from the source 318, which is a common source for the pulse generator 304 as well. As will be described hereinafter, the interface circuit 18F includes a plurality of switches to select outputs of different pulse widths and apply them to different ones of the conductors 213H.

The counter circuits 311A–311C are identical and are settable to provide the different duration pulses. The counter circuit 311A is shown in detail and includes a counter 306 and a selector switch 310, the outputs of the counter 306 being electrically connected to different ones of the contacts of the switch 310 and the armature being electrically connected to the conductor 313A.

The power supply 318 for the pulse generator 304 is electrically connected to a conductor 316 to a first of the contacts 314 and the rest of the contacts are electrically connected to the outputs of the counter 306. The conductor 313 is electrically connected to the reset input terminal of the counter 306 so that, when the switch connects a particular output of the counter, the counter counts to that output and then resets itself and at the same time applies a pulse through conductor 313A to the interface circuit 18F for use as a timing pulse under the control of an interval set by the position of the switch 310.

The pulse generator 304 applies signals to the pulse input terminals of the counter and sets a basic count frequency which determines the shortest time duration, with the time durations available on conductor 313A being multiples of that duration as set by the selector switch 310.

Figure 15:
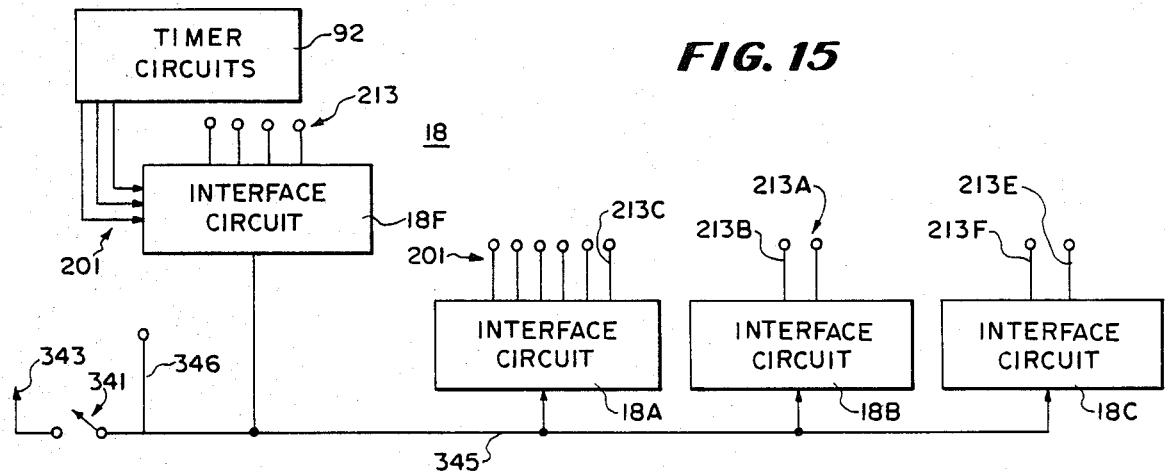
FIG. 15 is a block diagram of still another portion of the embodiment of FIG. 1.

In FIG. 15, there is shown a block diagram of the external control and mode selection system 18, having an on-off switch 341, a plurality of interface circuits 18A–18C and 18F, and the timer circuits 92. The on-off switch 341, when closed, electrically connects a source of power 343 to a conductor 345 for supplying power to: (1) conductor 346 for the power-connect circuits; and (2) the interface circuits 18A–18C and 18F.

While only four interface circuits 18A–18C and 18F are shown in FIG. 15, there are actually six such circuits 18A–18F in FIGS. 1–14 for selecting the response patterns described in connection with FIGS. 1–14. The manner in which the interface circuits are set to perform the selected functions is described below.

Figure 16:
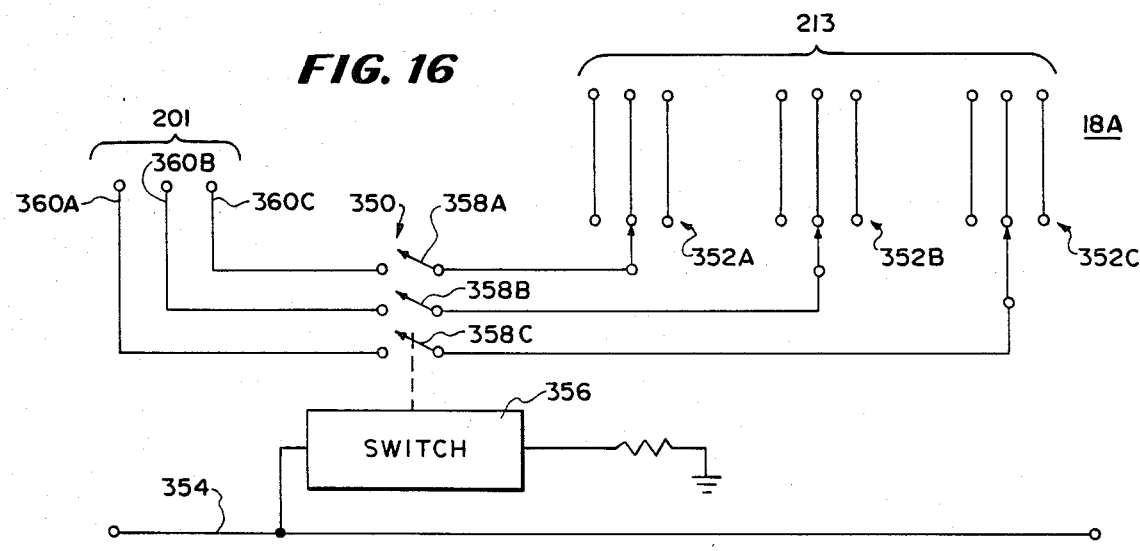
FIG. 16 is a schematic circuit diagram of a portion of the invention.

In FIG. 16, there is shown a schematic circuit diagram of a typical interface circuit 18A in simplified form, having an automatic power switch 350 and a plurality of manually settable switches 352A, 352B and 352C. To activate the interface circuit 18A when the switch 341 (FIG. 15) is closed, conductor 354 is electrically connected to a relay 356 of the switch 350.

The relay 356, when energized, closes a plurality of armatures 358A, 358B and 358C against corresponding contacts. The closing of these switches by energization of the switch 350 provides an electrical connection between the input terminals 360A–360C and the poles of the respective manual switches 352A–352C. Each of the manual switches 352A–352C may be moved against a different contact to provide an electrical connection between a selected one of the conductors 201 and a selected one of the conductors 213 electrically connected to the contacts of the manual switches.

With this arrangement, the interface circuits may be used to provide an electric contact between the conductors 201 and 213. The interface circuits 18A–18C (FIG. 15) contain substantially the same structure to enable electrical connection between the input conductors and output conductors as preset by a programmer.

While a hardware controller system 14 and an external control and mode selection system 18 have been disclosed in some detail, in the preferred embodiment the functions of the controller system 14 and the external control and mode selection system 18 are performed by standard microprocessor equipment because of the economy had reduced cost of such equipment. The hardware of FIGS. 10–16 has not been built but is described as a possible hardware embodiment. It is well known in the art how to program microprocessor equipment to perform the simple switching functions illustrated by the block diagrams and circuits (FIGS. 1–16).

In the preferred embodiment, the microprocessor is an RCA CDP1802D COSMAC microprocessor which may be purchased from RCA Corporation, Solid State Division, Somerville, N.J. 08876. It is described in its publications, Preliminary CDP 1802D, CDP1802CD, and "Operating Considerations for RCA Solid State Devices," Form No. 1CE-402, available from RCA Solid State Division, Box 3200, Somerville, N.J. 08876. It is used with the National Semiconductor MM58167 Microprocessor Compatible Real Time Clock, the 8-Bit Buffered Multiplying DAC sold by Analog Devices, available from Technical Sales Associates, Inc., 9211 Bond, P.O. Box 14842, Shawnee Mission, Kansas 66215, and the Intersil 1CL7109 12-Bit Binary A/D Converter for Microprocessor Interfaces available from Intersil, Inc., 10710 North Tantau Avenue, Cupertino, Ca. 95014.

Figure 17:
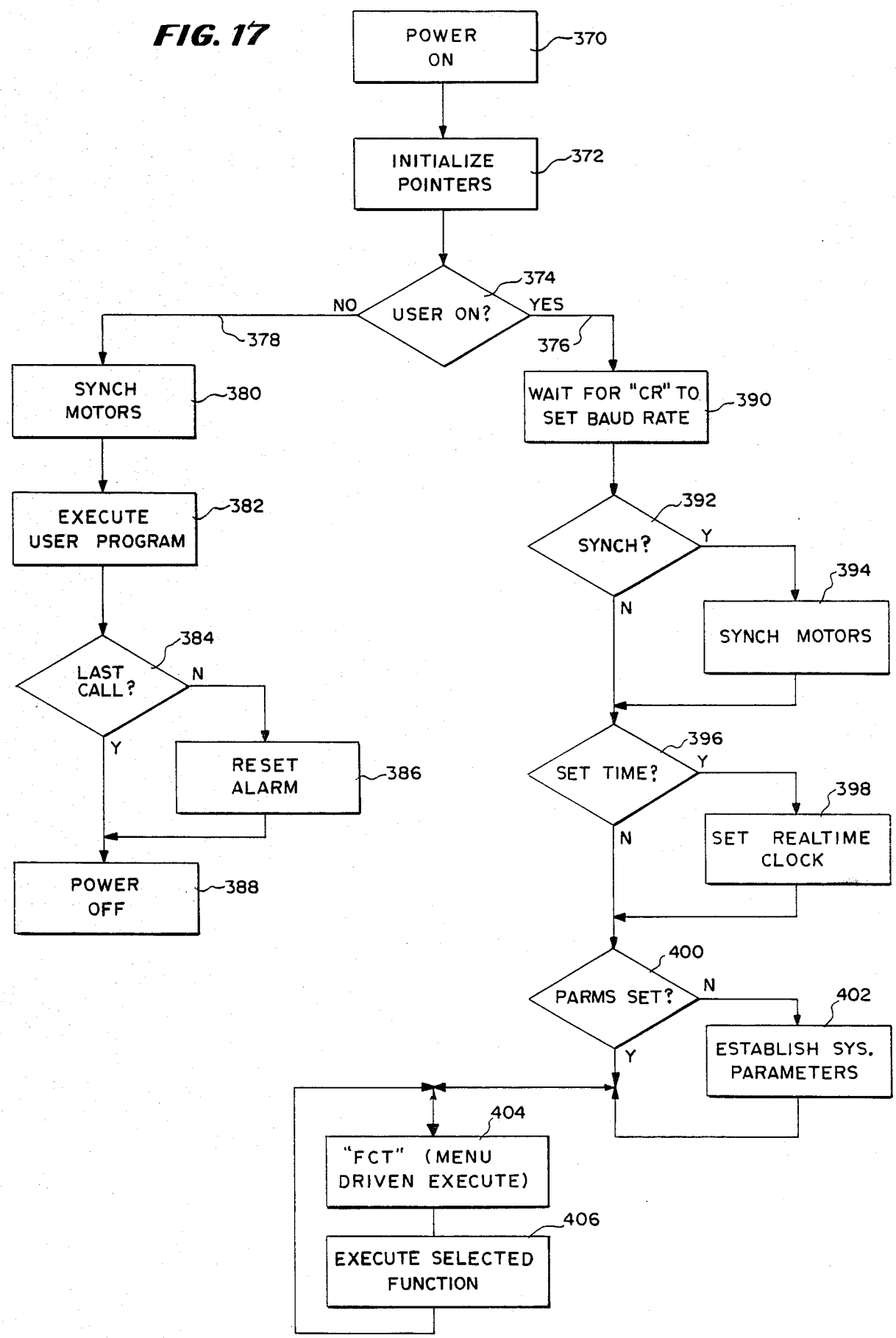
FIG. 17 is a flow diagram illustrating the operation of another embodiment of the invention.

As shown in FIG. 17, the algorithm for instrument operation includes the following microcomputer steps, which are: a power-on step 370 followed by a step 372 of initializing the pointers. These two steps are performed in the hardware embodiment by manually closing switches in the interface circuits to start operation and to indicate a beginning point for values that are to be used in the circuitry.

After the power has been turned on and the pointers initialized, the microprocessor program checks memory which records a switch indicating if a program mode or a normal mode is to be followed. The normal mode is directly under operator control and the program mode is automatic in response to a clock. This check is indicated at step 374 and, if normal mode is to be followed, the sequence indicated at 376 is followed and, if the program mode is indicated by a memory location showing timer actuation, then the branch of the program at 378 is followed.

In the second branch indicated at 378 for the program mode, two steps are indicated in sequence which are the synchronization of the motors at step 380 and the execution of the user program at step 382. These steps in the mechanical circuitry are the return-to-zero steps and the sequencing as determined by manual switches. The next step is a decision step indicating if there is still another delayed scan time as shown at step 384. If there is another scan, a step to reset the alarm as shown at 386 is followed. Finally, the power is turned off as shown by step 388.

If the branch 376 is followed in the normal mode, the microprocessor program waits until the band rate has been set. Once the rate has been set, the program checks to determine if the user desires synchronization as shown at step 392. If not, then they are synchronized as shown at step 394 and, if they are, the program proceeds to the next step. In the next step, a decision is made to set the time as shown at step 396. If it is not set, then the program proceeds to step 398 and the real time clock is set and, if it has been set, the program proceeds to the setting of the memory at step 400.

At step 400, the user makes a decision whether system parameters are set and, if the decision is that they are not set, it proceeds to step 402 to set the parameters and, if they are set, it proceeds to step 404. After step 404, two steps are executed and the program returns back to step 404. Those two steps in sequence are the step to obtain the micro instruction for executing the selected program and the step 406 to execute that function. This process continues under the selection and control of the operator until operations have been completed.

Obviously, other programs may be used for the same algorithm and many algorithms may be performed by the microprocessor. Moreover, any one of many different programmed microprocessors may be used to accomplish the same result as the hardware circuits of FIGS. 10–16.

As can be understood from the above description, the apparatus and method for measuring light of this invention has several advantages such as: (1) it is portable and may be used in the field; (2) it provides relatively precise measurements for spectroradiometry without temperature control; (3) it uses a relatively small amount of power; (4) it provides data readout in a number of different modes; (5) it is adaptable to remote measurement from a number of different sources such as through a cosine reflector, telescope, heliometer, spherical sensor or the like; and (6) it may be converted to a photoradiometer.

Although a preferred embodiment has been described with some particularity, many modifications and variations in the preferred embodiment may be made without deviating from the invention. Therefore, it is to be understood that, within the scope of the appended claims, the invention may be practiced other than as specifically described.

What is claimed is:

1. A portable spectroradiometer comprising:
   inlet means for receiving light to be sensed;
   diffuser means for diffusing the light to be sensed;
   filter means for sequentially passing each of a series of light wavelength bands constituting a scan while blocking other wavelengths;
   diffraction grating means for sequentially passing a similar plurality of wavelength bands constituting a scan with the wavelengths of the scan falling within falling within the range of 250 to 1150 nanometers in wavelength and with each of the bands within the scan having a bandwidth in the range of 2 to 15 nanometers in wavelength;
   means for synchronizing said filter means and diffraction grating means, whereby selected narrow bandwidths of light across a selected scan are passed by the diffraction grating means and the filter means removes stray high intensity light and higher harmonics of the light passed by the diffraction grating means;
   said rate of scan being in the range of 20 to 100 nanometers of wavelength per second;
   detection means for detecting the light passing through said inlet means, filter means and diffraction grating means;
   said detection means including a silicon photodetector, whereby an electrical signal of sufficient precision is received without special cooling within the narrow bandwidths;
   said inlet means, filter means and diffraction grating means having light-passing paths sufficiently large to pass sufficient light flux of at least 10 microwatts per square meter on the diffuser means to the silicon photodetector for each nanometer of bandwidth to obtain a useable electrical signal;
   said diffraction grating means including a holographic grating with a "f" number less than 5;
   means for digitizing said signal;
   means for storing said digitized signal; and
   said means for storing including a capacity of at least 30 kilobytes with a power requirement of no more than 2 watts of power for storage without scanning power, whereby said instrument may be portable while providing sufficiently precise measurements.

2. A portable spectroradiometer according to claim 1 further comprising:
   means for combining an electrical signal from said detection means for detecting while all said light is blocked from said silicon photodetector;
   means for subtracting the value of said signal received from said silicon photodetector from said sensed signal, whereby automatic instrument zeroing is provided; and
   said filter means being movable filter means which in one position blocks all light during scanning.

3. A portable spectrometer according to claim 2 in which said inlet means includes a light fiber formed of quartz and having at least a 50 percent packing density and a cone angle of at least 24 degrees.

4. A method of measuring radiation comprising the steps of:
   carrying a self-contained battery-powered spectroradiometer to a location where light is to be measured;
   applying light to a silicon photodetector at wavelengths within the range of between 250 to 1150 nanometers at a plurality of discrete bandwidths within the range of 2 to 15 nanometers at a scanning rate in the range of 20 to 100 nanometers per second;
   screening other wavelengths of light out with a diffraction grating and high-intensity harmonics of the light passed through the diffraction grating with a series of synchronized filters; and
   digitizing and storing the electrical signal from the silicon photodetector into a memory capable of storing at least 30 kilobytes and using less than 2 watts of power.

5. A method of measuring radiation in accordance with claim 4 in which the step of applying light to a silicon photodetector includes the step of periodically blocking all light and receiving a calibration electrical signal, digitizing the electrical signal and subtracting it from the electrical signal received at each of said plurality of scans.

6. A method according to claim 5 in which the step of applying said light includes the step of applying said light through a quartz fiber conductor bundle having a packing density of at least 50 percent and a cone angle of at least 24 degrees.

7. A method according to claim 6 in which the step of applying light includes the steps of repeatedly applying the same frequencies of light and finding the average of each of the electrical signals for each of the discrete wavelength bands in a plurality of scans.

8. Apparatus comprising:
   inlet means for receiving light to be sensed;
   means for sequentially passing each of a series of light wavelength bands falling within 250 to 1150 nanometers in wavelength and with each of the bands within the scan having a bandwidth in the range of 2 to 15 nanometers in wavelength constituting a scan while blocking other wavelengths;
   means for detecting the light passing through said inlet means and through said means for sequentially passing; and
   said detection means including a silicon photodetector, whereby an electrical signal of sufficient precision is received without special cooling within the narrow bandwidths.

9. Apparatus according to claim 8 in which said means for sequentially passing includes:
   a diffraction grating means for scanning at a rate of scan in the range of 20 to 100 nanometers of wavelength per second said diffraction grating means includes a diffraction grating having an aperture of at least 4.

10. Apparatus according to claim 8 in which said inlet means has diffusing means and a light-passing path between the diffusing means and the silicon photodetector capable of passing light outside of the noise level to the silicon photodetector from light on the diffuser means of at least 10 microwatts per square meter of diffuser means for each nanometer of bandwidth.

11. Apparatus according to claim 8 further comprising:
    means for digitizing said signal;
    means for storing said digitized signal; and
    said means for storing including at least 30 kilobytes of storage capacity with a power requirement of no more than 2 watts of power for storage without scanning power.

12. Apparatus according to claim 8 in which:
    said means for sequentially passing is a movable means which in one position blocks all light during scanning;
    said means for detecting includes means for obtaining an electrical signal from said means for detecting while all said light is blocked from said silicon photodetector; and
    means for subtracting the value of said signal received from said photodetector from said sensed signal, whereby automatic instrument zeroing is provided.

13. Apparatus according to claim 8 in which said inlet means includes a light fiber formed of quartz and having at least a 50 percent packing density and a cone angle of at least 24 degrees.

14. A method comprising the steps of:
    scanning frequencies of light for application to a silicon photodetector at wavelengths within the range of between 250 and 1150 nanometers at a plurality of discrete bandwidths within the range of 2 to 15 nanometers each and screening other wavelengths of light out; and
    digitizing and storing the electrical signal from the silicon photodetector into a memory capable of storing at least 30 kilobytes of information with less than 2 watts of power.

15. A method in accordance with claim 14 in which the step of scanning frequencies of light for application to a silicon photodetector includes the step of periodically blocking all light and receiving an error electrical signal and subtracting it from the measured signal.

16. A method according to claim 15 in which the step of scanning frequencies of said light includes the step of applying said light through a quartz fiber conductor bundle having a packing density of at least 50 percent and a cone angle of 24 degrees.

17. A method according to claim 16 in which the step of applying light includes the steps of repeatedly applying light of the same frequencies and finding the average of each of the electrical signals for each of the discrete wavelength bands in a plurality of scans.

18. Apparatus comprising:
    inlet means for receiving light to be sensed;
    means for sequentially passing each of a series of light wavelength bands falling within the range of 250 to 1150 nanometers in wavelength to form a sequential scan of wavelength bands with each of the bands within the scan having a bandwidth in the range of 2 to 15 nanometers in wavelength while blocking other wavelengths;
    means for detecting the light passing through said inlet means and through said means for sequentially passing;
    said detection means including a photodetector, whereby an electrical signal is received;
    means for digitizing said signal;
    means for recording said digitized signal;
    means for applying light from a source having a known spectrum to said inlet means;
    said means for recording including means for recording said digitized signals for said known source of the known spectrum value from said source; and
    means for comparing signals from an unknown source with said digitized signals from said known source and providing corresponding values of the spectrum from said unknown source.

19. Apparatus according to claim 18 comprising:
    said means for sequentially passing including scanning means for repeating each sequential scan of said wavelength bands at a rate of scan in the range of 20 to 100 nanometers of wavelength per second;
    said detection means including a silicon photodetector, whereby an electrical signal of sufficient precision is received without special cooling within the narrow bandwidths; and
    said inlet means including a diffusion means and a light path between said diffusion means and said silicon photodetector;
    said light path including filter means and diffraction grating means; and
    said light path being capable of passing at least sufficient light to be within the dynamic range of said silicon photodetector from an amount of light flow of at least 10 microwatts per square meter of diffuser means for each nanometer of bandwidth.

20. Apparatus according to claim 18 in which said inlet means includes a light fiber formed of quartz and having at least a 50 percent packing density and a cone angle of at least 24 degrees.

21. A method comprising the steps of:
    applying light to a photodetector at least at wavelengths within the range of between 250 and 1150 nanometers at a plurality of discrete bandwidths within the range of 2 to 15 nanometers from a source with a known spectrum;

screening other wavelengths of light out from said known source;

digitizing and storing the electrical signal from the known source in a calibration section of memory together with the value of the spectrum for the measurements;

applying light from sources with an unknown spectrum to the same photodetector at wavelengths within the range of between 250 and 1150 nanometers at a plurality of discrete bandwidths within the range of 2 to 15 nanometers;

screening other wavelengths of light out from said sources of unknown spectrums; and digitizing and correlating the electrical signal from the photoconductor from said source of unknown spectrum with said digitized signals from said known spectrum to obtain the corresponding values of the spectrum of the source having an unknown spectrum.

22. A method of measuring radiation in accordance with claim 21 in which the step of applying light includes the steps of:
applying light to a silicon photodetector;
periodically blocking all light to the photodetector;
receiving a drift electrical signal;
digitizing the electrical drift signal; and
subtracting it from the electrical signal received at each of said plurality of scans.

23. A method according to claim 22 in which the step of applying said light includes the step of applying said light through a quartz fiber conductor bundle having a packing density of at least 50 percent and a cone angle of at least 24 degrees.

24. A portable spectroradiometer comprising:
inlet means for receiving light to be sensed; means for sequentially passing each of a series of light wavelength bands falling within 250 to 1150 nanometers in wavelength and with each of the bands within the scan having a bandwidth in the range of 2 to 15 nanometers in wavelength constituting a scan while blocking other wavelengths;
means for detecting the light passing through said inlet means and through said means for sequentially passing;
said detection means including a photodetector, whereby an electrical signal is received;
means for digitizing said signal;
means for recording said digitized signal; and
means for storing including at least 30 kilobytes with a power requirement of no more than 2 watts of power for storage without scanning power, whereby said instrument may be portable while providing sufficiently precise measurements.

25. A portable spectrometer according to claim 24 in which said inlet means includes a light fiber formed of quartz and having at least a 50 percent packing density and a cone angle of at least 24 degrees.

26. A portable spectroradiometer according to claim 25 in which said means for detecting includes a silicon photodiode.

27. A method comprising the steps of:
carrying a self-contained battery-powered spectroradiometer to a location where light is to be measured;
applying light to a photodetector at certain wavelengths within the range of between 250 and 1150 nanometers at least one of a plurality of certain discrete bandwidths within the range of 2 to 15 nanometers.
screening other wavelengths of light out; and
digitizing and storing the electrical signal from the photodetector into a memory capable of storing at least 30 kilobytes with less than 2 watts of power.

28. A method of measuring radiation in accordance with claim 27 in which the step of applying light to a photodetector includes the steps of:
periodically blocking all light;
receiving a drift electrical signal;
digitizing the drift electrical signal; and
subtracting the drift electrical signal from the electrical signal received at each of said plurality of scans.

29. A method according to claim 28 in which the step of applying said light includes the step of applying said light through a quartz fiber conductor bundle having a packing density of at least 50 percent and a cone angle of at least 24 degrees.

30. A method according to claim 29 in which the step of measuring radiation includes the step of finding the average of each of the electrical signals for each of the discrete wavelength bands in a plurality of scans.

* * * * *